US011390656B2

(12) United States Patent
Liu et al.

(10) Patent No.: US 11,390,656 B2
(45) Date of Patent: Jul. 19, 2022

(54) PROGRANULIN (PGRN) FRAGMENTS AND DERIVATIVES FOR TREATMENT OR ALLEVIATION OF LYSOSOMAL STORAGE DISEASES

(71) Applicant: NEW YORK UNIVERSITY, New York, NY (US)

(72) Inventors: Chuanju Liu, Orange, CT (US); Jinlong Jian, River Edge, NJ (US); Qingyun Tian, Forest Hills, NY (US)

(73) Assignee: New York University, New York, NY (US)

( * ) Notice: Subject to any disclaimer, the term of this patent is extended or adjusted under 35 U.S.C. 154(b) by 481 days.

(21) Appl. No.: 15/749,672

(22) PCT Filed: Aug. 4, 2016

(86) PCT No.: PCT/US2016/045560
§ 371 (c)(1),
(2) Date: Feb. 1, 2018

(87) PCT Pub. No.: WO2017/024137
PCT Pub. Date: Feb. 9, 2017

(65) Prior Publication Data
US 2018/0222952 A1    Aug. 9, 2018

Related U.S. Application Data

(60) Provisional application No. 62/200,895, filed on Aug. 4, 2015.

(51) Int. Cl.
| | |
|---|---|
| *C07K 14/475* | (2006.01) |
| *A61K 38/18* | (2006.01) |
| *A61K 38/47* | (2006.01) |
| *A61P 3/00* | (2006.01) |
| *A61K 38/17* | (2006.01) |
| *C12Q 1/68* | (2018.01) |

(52) U.S. Cl.
CPC ........ *C07K 14/475* (2013.01); *A61K 38/1709* (2013.01); *A61K 38/18* (2013.01); *A61K 38/47* (2013.01); *A61P 3/00* (2018.01); *C12Q 1/68* (2013.01); *C12Y 302/01045* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 8,362,218 B2 | 1/2013 | Liu | |
| 8,871,915 B2 | 10/2014 | Liu | |
| 10,357,542 B2* | 7/2019 | Liu | A61P 3/00 |
| 2005/0175616 A1 | 8/2005 | Kiener | |
| 2008/0199470 A1* | 8/2008 | Cheung | G01N 33/57438 424/138.1 |
| 2010/0324127 A1* | 12/2010 | Kay | A61K 31/70 514/44 R |
| 2013/0157945 A1 | 6/2013 | Liu | |
| 2013/0230506 A1 | 9/2013 | Jensen et al. | |
| 2015/0268241 A1* | 9/2015 | Egland | G01N 33/564 514/789 |
| 2018/0147300 A1* | 5/2018 | Park | C12N 9/2405 |

FOREIGN PATENT DOCUMENTS

| | | | | |
|---|---|---|---|---|
| EP | 266476 B1 | | 12/2018 | |
| WO | WO 2004/023973 | * | 3/2004 | |
| WO | WO 2008/019187 | * | 2/2008 | |
| WO | 2010/120374 A2 | | 10/2010 | |
| WO | WO 2011/140086 | * | 11/2011 | ............. C07K 14/78 |
| WO | WO 2015/096858 | * | 7/2015 | ............. G01N 33/68 |
| WO | 2015/119989 A1 | | 8/2015 | |

OTHER PUBLICATIONS

Jian et al. 'Progranulin Recruits HSP70 to β-Glucocerebrosidase and Is Therapeutic Against Gaucher Disease.' WEBioMedicine 13:212-224, 2016.*
Aerts, J. M. et al (2011) Biomarkers in the diagnosis of lysosomal storage disorders: proteins, lipids, and inhibodies Journal of inherited metabolic disease 34, 605-619.
Aerts, J. M. et al (1988) Glucocerebrosidase, a lysosomal enzyme that does not undergo oligosaccharide phosphorylation Biochimica et biophysica acta 964, 303-308.
Ahmed, Z. et al (2010) Accelerated lipofuscinosis and ubiquitination in granulin knockout mice suggest a role for progranulin in successful aging The American journal of pathology 177, 311-324, doi:10.2353/ajpath.2010.090915.
Almeida et al (2011) Progranulin, a glycoprotein deficient in frontotemporal dementia, is a novel substrate of several protein disulfide isomerase family proteins PloS one 6, e26454, doi:10.1371/journal.pone.0026454.
Baba T et al (1993) Acogranin, an acrosomal cysteine-rich glycoprotein, is the precursor of the growth-modulating peptides, granulins, and epithelins, and is expressed in somatic as well as male germ cells Mol Reprod Dev 34(3):233-243.
Baker, M. et al (2006) Mutations in progranulin cause tau-negative frontotemporal dementia linked to chromosome 17 Nature 442, 916-919, doi:10.1038/nature05016.
Bateman A et al (1990) Granulins, a novel class of peptide from leukocytes Biochem Biophys Res Comm 173(3):1161-1168.
Bateman et al (2009) The granulin gene family: from cancer to dementia. BioEssays News and Reviews in molecular, cellular and developmental biology 31, 1245-1254, doi:10.1002/bies.200900086.

(Continued)

*Primary Examiner* — Nora M Rooney
(74) *Attorney, Agent, or Firm* — Hoffmann & Baron, LLP

(57) ABSTRACT

The present invention provides peptides, compositions and methods for treatment and alleviation of lysosomal storage diseases and their diagnosis and treatment, including Gaucher's Disease, and particularly which utilize one or more progranulin (PGRN) derivative or fragment, particularly fragment ND7/Pcgin.

24 Claims, 20 Drawing Sheets

Specification includes a Sequence Listing.

(56) References Cited

OTHER PUBLICATIONS

Beutler, E. (1991) Gaucher's disease The New England journal of medicine 325, 1354-1360, doi:10.1056/NEJM199111073251906.
Beutler E & Grabowski GA (2001) Gaucher Disease. in The Metabolic and Molecular Basis of Inherited Disease CR Scriver et al eds. McGraw Hill, NY pp. 3635-3668.
Blanz, J. et al (2010) Disease-causing mutations within the lysosomal integral membrane protein type 2 (LIMP-2) reveal the nature of binding to its ligand beta-glucocerebrosidase Human molecular genetics 19, 563-572, doi:10.1093/hmg/ddp523.
Brady et al (1965) Metabolism of Glucocerebrosides. Ii. Evidence of an Enzymatic Deficiency in Gaucher's Disease Biochemical and biophysical research communications 18, 221-225.
Brooks DA (1999) Immune response to enzyme relacement therapy in lysosomal storage disorder patients and animal models Mole Genet Metab 68(2):268-275.
Cenik B et al (2012) Progranulin: a proteolytically processed protein at the crossroads of inflammation and neurodegeneration J Biol Chem 287(39):32298-32306.
Chen et al (2018) Progranulin associates with hexosaminidase A and ameliorates GM2 ganglioside accumulation and lysosomal storage in Tay-Sachs disease, Journal of Molecular Medicine 96:1359-1373.
Cruts, M. et al (2006) Null mutations in progranulin cause ubiquitin-positive frontotemporal dementia linked to chromosome 17q21 Nature 442, 920-924, doi:10.1038/nature05017.
Daniel R et al (2000) Cellular localization of gene expression for progranulin J Histochem Cytochem 48(7):999-1009.
Davidson B et al (2004) Granulin-epithelin precursor is a novel prognostic marker in ovarian carcinoma Cancer 100(10):2139-2147.
Eblan, M.J et al (2005) The glucocerebrosidase gene and Parkinson's disease in Ashkenazi Jews The New England Journal of medicine 352, 728-731; author reply 728-731, doi:10.1056/NEJM200502173520719.
Fabrega S. et al (2000) Human glucocerebrosidase: heterologous expression of active site mutants in murine null cells. Glycobiology 10, 1217-1224.
Farfel-Becker et al (2011) Animal models for Gaucher disease research Disease models & mechanisms 4, 746-752, doi:10.1242/dmm.008185.
Gaspar, P. et al (2014) Action myoclonus-renal failure syndrome: diagnostic applications of activity-based probes and lipid analysis Journal of lipid research 55, 138-145, doi:10.1194/jlr.M043802.
Gonzalez, et al (2003) A novel interaction between perlecan protein core and progranulin: potential effects on tumor growth J Biol Chem 278, 38113-38116.
Gotzl, J. K. et al (2014) Common pathobiochemical hallmarks of progranulin-associated frontotemporal lobar degeneration and neuronal ceroid lipofuscinosis Acta Neuropathol, doi:10.1007/s00401-014-1262-6.
Grabowski GA (2008) Phenotype, diagnosis, and treatment of the Gaucher's disease Lancet 372(9645):1263-1271.
Grabowski, G. A. (2012) Gaucher disease and other storage disorders. Hematology / the Education Program of the American Society of Hematology American Society of Hematology. Education Program 2012, 13-18, doi:10.1182/asheducation-2012.1.13.
He, Z and Bateman, A (1999) Progranulin gene expression regulates epithelial cell growth and promotes tumor growth in vivo. Cancer Res 59, 3222-3229.
He, Z et al (2002) Progranulin (PC-cell-derived growth factor/ acrogranin) regulates invasion and cell survival. Cancer Res 62, 5590-5596.
He Z et al (2003) Progranulin (granulin-epithelin precursor, PC-cell-derived growth factor, acrogranin) mediates tissue repair and tumorigenesis J Mol Med 81(10):600-612).
He Z et al (2003) Progranulin is a mediator of the wound response Nat Med 9(2):225-229.
Holler et al (2016) Trehalose upregulates progranulin expression in human and mouse models of GRN haploinsufficiency: a novel therapeutic lead to treat frontotemporal dementia Molecular Neurodegeneration. vol. 11, pp. 1-17.
Hoque, M et al (2003) The growth factor granulin interacts with cylin T1 and modulates P-TEFb-dependent transcription Mol Cell Biol 23(5):1688-1702).
Hrabal et al (1996) The hairpin stack fold, a novel protein architecture for a new family of protein growth factors Nat Struct Biol 3, 747-752.
Hu, F. et al (2010) Sortilin-mediated endocytosis determines levels of the frontotemporal dementia protein, progranulin Neuron 68, 654-667.
Ingemann, et al (2014) Lysosomal Storage Diseases and the Heat Shock Response: Convergences and Therapeutic Opportunities. Journal of lipid research, doi:10.1194/jlr.R048090.
Jian et al (2013) Insights into the role of progranulin in immunity, infection, and inflammation. Journal of leukocyte biology 93, 199-208, doi:10.1189/jlb.0812429 (2013).
Jian, J. et al (2013) Progranulin directly binds to the CRD2 and CRD3 of TNFR extracellular domains FEBS letters, doi:10.1016/j.febslet.2013.09.024.
Jones MB et al (2003) The granulin-epithelin precursor: a putative new growth factor for ovarian cancer Gynecol Oncol 88(1 pt2):S136-139.
Kirkegaard, T. et al (2010) Hsp70 stabilizes lysosomes and reverts Niemann-Pick disease-associated lysosomal pathology Nature 463, 549-553, doi:10.1038/nature08710.
Kolodny E, et al (2011) ALBC Newsletter (Pittsboro, North Carolina, USA: American Livestock Breeds Conservancy).
Leverenz, J. B. et al (2007) A novel progranulin mutation associated with variable clinical presentation and tau, TDP43 and alpha-synuclein pathology Brain : a journal of neurology 130, 1360-1374, doi:10.1093/brain/awm069.
Li, M. et al (2014) Progranulin is required for proper ER stress response and inhibits ER stress-mediated apoptosis through TNFR2 Cell Signal 26, 1539-1548, doi:10.1016/j.cellsig.2014.03.026.
Liu,et al (2014) Progranulin-Derived Atsttrin Directly Binds to TNFRSF25 (DR3) and Inhibits TNF-Like Ligand 1A (TL1A) Activity PloS one 9, e92743, doi:10.1371/journal.pone.0092743.
Lu, R et al (2000) Inhibition of PC cell-derived growth factor (PCDGF, epithelin/granulin precursor) expression by antisense PCDGF cDNA transfection inhibits turmorigenicity of the human breast carcinoma call line MDA-MB-468 Proc Natl Acad Sci USA 97(8)3993-3998.
Lu, J. et al (2011) Histone deacetylase inhibitors prevent the degradation and restore the activity of glucocerebrosidase in Gaucher disease. Proceedings of the National Academy of Sciences of the United States of America 108, 21200-21205, doi:10.1073/pnas.1119181109.
Mazzulli, J. R. et al (2011) Gaucher disease glucocerebrosidase and alpha-synuclein form a bidirectional pathogenic loop in synucleinopathies Cell 146, 37-52, doi:10.1016/j.cell.2011.06.001 (2011).
Miu, T. W. et al (2008) Chemical and biological approaches synergize to ameliorate protein-folding diseases Cell 134, 769-781, doi:10.1016/j.cell.2008.06.037.
Neculai, D. et al (2013) Structure of LIMP-2 provides functional insights with implications for SR-BI and CD36 Nature 504, 172-176, doi:10.1038/nature12684.
Nguyen, AD et al (2013) Progranulin: at the interface of neurodegenerative and metabolic diseases Traends Endocrinol Metab 24(12):597-606.
Petkau et al (2014) Progranulin in neurodegenerative disease Trends in neurosciences, doi:10.1016/j.tins.2014.04.003.
Platt et al (2012)The cell biology of disease: lysosomal storage disorders: the cellular impact of lysosomal dysfunction The Journal of cell biology 199, 723-734.
Platt, F. M. (2014) Sphingolipid lysosomal storage disorders Nature 510, 68-75.
Porter, BF, et al (2011) Pathology of GM2 gangliosidosis in Jacob sheep Vet Pathol 48(3): 807-813.
Prabakaran, T. et al (2012) Mannose 6-phosphate receptor and sortilin mediated endocytosis of alpha-galactosidase A in kidney endothelial cells PloS one 7, e39975.

(56) References Cited

OTHER PUBLICATIONS

Reczek, D. et al (2007) LIMP-2 is a receptor for lysosomal mannose-6-phosphate-independent targeting of beta-glucocerebrosidase Cell 131, 770-783.
Rothman, et al (2011) Molecular mechanism of protein folding in the cell Cell 146, 851-854.
Sun, Y et al (2005) Gaucher disease mouse models: point mutations at the acid beta-glucosidase locus combined with low-level prosaposin expression lead to disease variants J Lipid Res 46:2102-2113.
Saftig et al (2009) Lysosome biogenesis and lysosomal membrane proteins: trafficking meets function. Nature reviews. Molecular cell biology 10, 623-635.
Tanaka et al (2013) Increased lysosomal biogenesis in activated microglia and exacerbated neuronal damage after traumatic brain injury in progranulin-deficient mice Neuroscience 250, 8-19.
Tanaka et al (2014) Possible involvement of lysosomal dysfunction in pathological changes of the brain in aged progranulin-deficient mice Acta neuropathologica communications 2, 78.
Tang, W. et al (2011) The growth factor progranulin binds to TNF receptors and is therapeutic against inflammatory arthritis in mice Science 332, 478-484.
Torres, PA, et al (2010) Tay-Sachs disease in Jacob sheep Mol Genet Metab 101 (4):357-363.
Van Sweiten, JC et al. (2008) Mutations in progranulin (GRN) within the spectrum of clinical and pathological phenotypes of frontotemporal dementia Lancet Neurol 7(10):965-974).
Van Weely, S. et al (1990) Function of oligosaccharide modification in glucocerebrosidase, a membrane-associated lysosomal hydrolase European journal of biochemistry / FEBS 191, 669-677.
Vitner, E. B. et al. (2014) RIPK3 as a potential therapeutic target for Gaucher's disease Nat Med 20, 204-208.
Wang, W et al (2003) PC cell-derived growth factor (granulin precursor) expression and action in human multiple myeloma Clin Cancer Res 9(6):2221-2228.
Wei, H. et al (2008) ER and oxidative stresses are common mediators of apoptosis in both neurodegenerative and non-neurodegenerative lysosomal storage disorders and are alleviated by chemical chaperones Human molecular genetics 17, 469-477.
Witte, M. D. et al (2010) Ultrasensitive in situ visualization of active glucocerebrosidase molecules Nature chemical biology 6, 907-913.
Wright, WE et al (1989) Myogenin, a factor regulating myogenesis, has a domain homologous to MyoD Cell 56(4):607-617.
Xu, Y et al (2010) Comparative therapeutic effects of velaglucerase alfa and imiglucerase in a Gaucher disease mouse model PloS one 5, e10750.
Yang, C. et al (2014) Celastrol increases glucocerebrosidase activity in Gaucher disease by modulating molecular chaperones Proceedings of the National Academy of Sciences of the United States of America 111, 249-254.
Yin, F et al (2010) Behavioral deficits and progressive neuropathology in progranulin-deficient mice: a mouse model of frontotemporal dementia FASEB J. 24(12):4639-4647.
Yin, F et al (2010) Exaggerated inflammation, impaired host defense, and neuropathology in progranulin-deficient mice. J Exp Med 207(1):117-128.
Zanocco-Marani, T et al (1999) Biological activities and signaling pathways of the granulin/epitelin precursor Cancer Res 59(20):5331-5340.
Zhao et al (2003) Gaucher's disease: identification of novel mutant alleles and genotype-phenotype relationships Clin Genet 64(1):57-64.
Zheng, Y et al (2011) C-terminus of progranulin interacts with the beta-propeller region of sortilin to regulate progranulin trafficking. PloS one 6, e21023.
Zhou J et al (1993) Purification of an autocrine growth factor homologous with mouse epithelin precursor from a highly tumorigenic cell line J Biol Chem 268(15):10863-10869.
Zhu, J. et al (2002) Conversion of proepithelin to epithelins: roles of SLPI and elastase in host defense and wound repair. Cell 111, 867-878.

\* cited by examiner

Figure 5
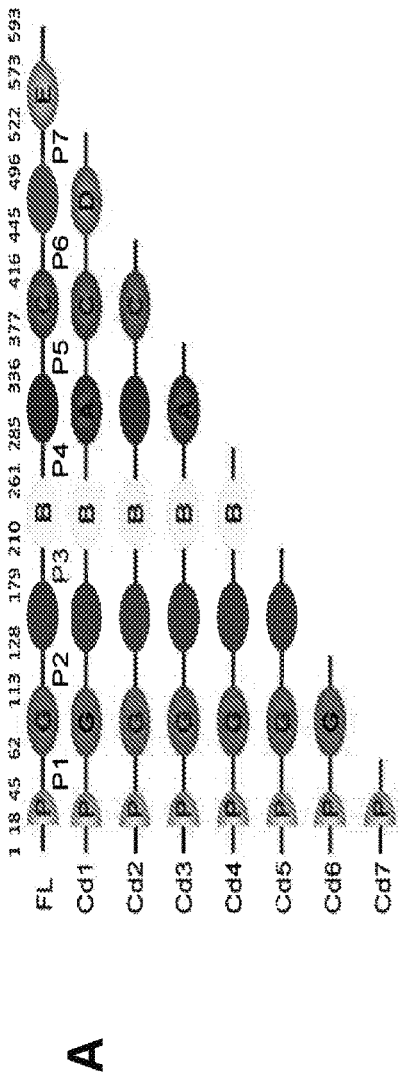

Human PGRN

```
  1  MWTLVSWVALTAGLVAGTRCPDGQFCPVACCLDPGGASYSCCRPLLDKWPTTLSRHLGGP
 61  CQVDAHCSAGHSCIFTVSGTSSCCPFPEAVACGDGHHCCPRGFHCSADGRSCFQRSGNNS
121  VGAIQCPDSQFECPDFSTCCVMVDGSWGCCPMPQASCCEDRVHCCPHGAFCDLVHTRCIT
181  PTGTHPLAKKLPAQRTNRAVALSSSVMCPDARSRCPDGSTCCELPSGKYGCCPMPNATCC
241  SDHLHCCPQDTVCDLIQSKCLSKENATTDLLTKLPAHTVGDVKCDMEVSCPDGYTCCRLQ
301  SGAWGCCPFTQAVCCEDHIHCCPAGFTCDTQKGTCEQGPHQVPWMEKAPAHLSLPDPQAL
361  KRDVPCDNVSSCPSSDTCCQLTSGEWGCCPIPEAVCCSDHQHCCPQGYTCVAEGQCQRGS
421  EIVAGLEKMPARRASLSHPRDIGCDQHTSCPVGQTCCPSLGGSWACCQLPHAVCCEDRQH
481  CCPAGYTCNVKARSCEKEVVSAQPATFLARSPHVGVKDVECGEGHFCHDNQTCCRDNRQG
541  WACCPYRQGVCCADRRHCCPAGFRCAARGTKCLRREAPRWDAPLRDPALRQLL
```

B

Mouse PGRN

```
  1  MWILVSWLALVARLVAGTQCPDGQFCPVACCLDQGGANYSCCNPLLDTWPIITSRRLDGS
 61  CQIRDHCPDGYSCLLTVSGTSSCCPFSEGVSCDDGQHCCPRGFHCSADGKSCSQISDSLL
121  GAVQCPGSQFECPDSATCCIMIDGSWGCCPMPQASCCEDRVHCCPHGASCDLVHTRCISP
181  TGTHPLLKKFPAQRTNRAVASFSVVCPDAKTQCPDDSTCCELPTGKYGCCPMPNAICCSD
241  HLHCCPQDTVCDLIQSKCISKDYTTDLMTKLPGYPVNEVKCDLEVSCPDGYTCCRLNTGA
301  WGCCPFTKAVCCEDHIHCCPAGFQCHTETGTCELGVLQVPWMKKVTASLSLPDPQILKND
361  VPCDDFSSCPSNNTCCRLSSGDWGCCPMPEAVCCLDHQHCCPQGFKCMDEGYCQKGDRMV
421  AGLEKMPVRQTTLLQHGDIGCDQHTSCPVGQTCCPSLKGSWACCQLPHAVCCEDRQHCCP
481  AGYTCNVKARTCEKDAGSVQPSMDLTFGSKVGNVECGAGHFCHDNQSCCKDSQGGWACCP
541  YVKGVCCRDGRHCCPIGFHCSAKGTKCLRKKTPRWDILLRDPAPRPLL
```

Figure 19

```
Human  EKEVVSAQPATELARSPHVGVKDVECGEGHFCHDNQTCCRDNRQGWACCPY
Mouse  EKDAGSVQPSMDLTFGSKVG-NVECGAGHFCHDNQSCCKDSQGWACCPY Human  RQGVCCADRRHCCPAGFRCAARGTKCLRREAPRWDAPLRDPALRQLL
Mouse  VKGVCCRDGRHCCPIGFHCSAKGTKCLRKKTPRWDILLRDPAPRPLL
```

PROGRANULIN (PGRN) FRAGMENTS AND DERIVATIVES FOR TREATMENT OR ALLEVIATION OF LYSOSOMAL STORAGE DISEASES

CROSS REFERENCE TO RELATED APPLICATIONS

The present application is a National Stage Application claiming priority from co-pending PCT Application No. PCT/US2016/045560 filed Aug. 4, 2016, which in turn, claims priority from U.S. Provisional Application Ser. No. 62/200,895 filed Aug. 4, 2015. Applicants claim the benefits of 35 U.S.C. § 120 as to the PCT Application and priority under 35 U.S.C. § 119 as to the said U.S. Provisional application, and the entire disclosures of all applications are incorporated herein by reference in their entireties.

FIELD OF THE INVENTION

The present invention relates generally to lysosomal storage diseases and their diagnosis and treatment, including Gaucher's Disease, and particularly to therapeutic aspects thereof which utilize a fragment or derivative of progranulin (PGRN).

BACKGROUND OF THE INVENTION

Progranulin (PGRN) is a multifunctional growth factor, also known as PC-cell-derived growth factor (PCDGF), acrogranin, Granulin/epithelin precursor (GEP), proepithelin (PEPI), or GP80, and was first purified as a growth factor from conditioned tissue culture media (Wright W E et al (1989) Cell 56(4):607-617; Zhou J et al (1993) J Biol Chem 268(15):10863-10869). PGRN is a 593-amino-acid secreted glycoprotein with an apparent molecular weight of 88 kDa. PGRN contains seven and a half repeats of a cysteine-rich motif $(CX_{5-6}CX_5CCX_8CCX_6CCXDX_2HCCPX_4CX_{5-6}C)$ (SEQ ID NO:1) in the order P-G-F-B-A-C-D-E, where A-G are full repeats and P is a half motif (FIG. 2).

PGRN has multiple physiological and pathological functions in development, would healing, anti-inflammation, neuron system disorders, as well as cancer. PGRN (GEP) is abundantly expressed in rapidly cycling epithelial cells, in cells of the immune system, and in neurons (Baba T et al (1993) Mol Reprod Dev 34(3):233-243; Daniel R et al (2000) Histochem Cytochem 48(7):999-1009). High levels of GEP expression are also found in several human cancers and contribute to tumorigenesis in diverse cancers, including breast cancer, clear cell renal carcinoma, invasive ovarian carcinoma, glioblastoma, adipocytic teratoma, and multiple myeloma (Davidson B et al (2004) Cancer 100(10):2139-2147; Bateman A et al (1990) Biochem Biophys Res Comm 173(3):1161-1168; Gonzales E M et al (2003) J Biol Chem 278(40):38113-38116; He A and Bateman A (2003) J Mol Med 81(10:600-612; Jones M B et al (2003) Gynecol Oncol 88(1 pt2):5136-139; Wang W et al (2003) Clin Cancer Res 9(6):2221-2228). PGRN was also found to be localized inside cells and to directly modulate intracellular activities (Daniel R et al (2000) Histochem Cytochem 48(7):999-1009; Hoque M et al (2003) Mol Cell Biol 23(5):1688-1702). Mutations of PGRN were found to cause frontotemporal lobular degeneration (FTLD) (Baker M et al (2006) Nature 442:916-919; Cruts M et al (2006) Nature 442:920-924). Since the initial FTLD studies, 70 pathogenic mutations of PGRN have been reported to cause FTLD (Van Sweiten J C et al (2008) Lancet Neurol 7(10):965-974).

Several PGRN-associated partners have been reported and found to affect PGRN action in various processes. One example is the secretory leukocyte protease inibitor (SLPI). Elastase digests PGRN in the intergranulin linkers with the generation of granulin peptides. SLPI blocks this proteolysis either by directly binding to elastase or by sequestering granulin peptides from the enzyme (Zhu J et al (2002) Cell 111(6):867-878). PGRN was also found to bind to Sortilin and mediate neurite growth (Hu F et al (2010) Neuron 68:654-667).

Recently, PGRN and PGRN peptides, particularly including the peptide denoted atsttrin, were identified as modulators of TNF/TNFR activity and signaling, and demonstrated to inhibit or block TNF-mediated signaling or response, including TNF-α-induced inflammatory arthritis (Tang W et al (2011) Science 332:478-484; WO 2010120374). Atsttrin is a PGRN-derived engineered protein (Antagonist of TNF/TNFR Signaling via Targeting TNF Receptors), comprising combinations of half units of PGRN units A, C and F in combination with linker units P3, P4 and P5 (U.S. Pat. No. 8,362,218; WO 2010120374). Atsttrin provides a PGRN-derived active peptide having overlapping activity and capability with the full length PGRN molecule. U.S. Pat. No. 8,362,218 and PCT publication WO 2010120374 describe PGRN-derived peptides comprising a combination of half units of progranin/granulin units, wherein at least one half unit is ½ F, and linker units, particularly at least two linker units.

Lysosomal Storage Diseases

Lysosomes are subcellular organelles responsible for the physiologic turnover of cell constituents. They contain catabolic enzymes, which require a low pH environment in order to function optimally. Lysosomal storage diseases (LSD) describe a heterogeneous group of dozens of rare inherited disorders characterized by the accumulation of undigested or partially digested macromolecules, which ultimately results in cellular dysfunction and clinical abnormalities. LSDs result from gene mutations in one or more of lysosomal enzymes, resulting in accumulation of the enzyme substrates in lysosomes. Organomegaly, connective-tissue and ocular pathology, and central nervous system dysfunction may result. Classically, lysosomal storage diseases encompassed enzyme deficiencies of the lysosomal hydrolases. More recently, the concept of lysosomal storage disease has been expanded to include deficiencies or defects in proteins necessary for the normal post-translational modification of lysosomal enzymes, activator proteins, or proteins important for proper intracellular trafficking between the lysosome and other intracellular compartments.

Over 50 lysosomal storage diseases have been described. The age of onset and clinical manifestations may vary widely among patients with a given lysosomal storage disease, and significant phenotypic heterogeneity between family members carrying identical mutations has been reported. Lysosomal storage diseases are generally classified by the accumulated substrate and include the sphingolipidoses, oligosaccharidoses, mucolipidoses, mucopolysaccharidoses (MPSs), lipoprotein storage disorders, lysosomal transport defects, neuronal ceroid lipofuscinoses and others. FIG. 1 depicts pathways for glycosphingolipids and indicates the altered metabolic enzymes associated with different lysosomal storage diseases.

The most common of the LSDs is Gaucher's Disease, which involves dysfunctional metabolism of sphingolipids and results from hereditary deficiency of the enzyme glucocerebrosidase. Glucocerebrosidase enzyme acts on the fatty acid glucosylceramide and when the enzyme is defective, glucosylceramide accumulates particularly in white blood cells, most often macrophages. Over 300 unique mutations of the glycocerebrosidase encoding gene GBA1 have been identified in Gaucher's Disease (Beutler E and Grabowski G A (2001) Gaucher Disease. in The Metabolic and Molecular Basis of Inherited Disease CR Scriver et al eds. McGraw Hill, N.Y. pp 3635-3668; Grabowski G A (2008) Lancet 372(9645):1263-1271; Zhao et al (2003) Clin Genet 64(1):57-64). Glucosylceramide can collect in the spleen, liver, kidneys, lungs, brain and bone marrow.

Gaucher's Disease (GD) falls into three subtypes, with varying pathology and severity. Type I (or non-neuropathic type) is the most common form of the disease, with an incidence of 1 in 50,000 live births of Ashkenazi Jewish heritage. Type I patients have hepatosplenomegaly. The brain is generally not affected pathologically, and depending on disease onset and severity, type 1 patients may live well into adulthood. Many patients have a mild form of the disease or may not show any symptoms. Type I is associated genetically with a GBA1 gene mutation N370S homozygote. Type II (or acute infantile neuropathic Gaucher's disease), begins within 6 months of birth and has an incidence rate of approximately 1 in 100,000 live births. Type II patients have an enlarged liver and spleen, extensive and progressive brain damage, eye movement disorders, spasticity, seizures, limb rigidity, and a poor ability to suck and swallow. Type II patients suffer from serious convulsions, hypertonia, mental retardation and apnea. Affected children usually die by age 2. Type II GD is associated with GBA1 mutation alleles including GBA1 mutation L444P. Type III GD, a chronic neuropathic form, can begin at any time in childhood or even in adulthood, and occurs in approximately 1 in 100,000 live births. It is characterized by slowly progressive but milder neurologic symptoms compared to the acute or type II GD. Major symptoms include an enlarged spleen and/or liver, seizures, poor coordination, skeletal irregularities, eye movement disorders, blood disorders including anemia and respiratory problems. Type III patients suffer from muscle twitches known as myoclonus, convulsions, dementia and ocular muscle apraxia. Patients often live into their early teen years and adulthood. The genetics and any specific GBA1 mutations associated with Type III GD are not clear.

Diagnostic indicators for Gaucher's Disease include increased alkaline phosphatase (ALP), angiotensin-converting enzyme (ACE) and immunoglobulin levels. Alternatively or in addition, cell analysis showing "crinkled paper" cytoplasm and glycolipid-laden macrophages, which are also called "Gaucher's cells" are cellular hallmarks of GD. Mutations in the GBA1 gene are also evaluated, particularly those known to be associated with the disease and Types as noted above. GBA1 mutational analysis can be valuable particularly in families at risk of GD due to family history or that are carriers of GBA1 mutations.

Therapy for LSDs includes enzyme replacement therapy to replace the disease mutant enzyme. Enzyme replacement therapy (ERT) and substrate reduction therapy (SRT) may be applicable for peripheral manifestations in patients with Gaucher disease types I and III, Fabry disease, mucopolysaccharidosis I (Hurler, Hurler-Scheie, and Scheie syndromes), mucopolysaccharidosis II (Hunter syndrome), mucopolysaccharidosis VI (Maroteaux-Lamy syndrome), and Pompe disease. Efforts are underway to develop enzyme replacement options for several other disorders. TABLE 1 provides ERTs being evaluated or approved for treatment of certain LSDs. Exemplary therapies, including ERT, for Gaucher's Disease are listed in TABLE 2. Thus far, ERT has been largely unsuccessful in improving central nervous system manifestations of the lysosomal storage diseases, possibly due to difficulty in penetrating the blood-brain barrier. This has led to active clinical trials evaluating the safety and efficacy of intrathecal enzyme delivery in several lysosomal storage diseases. Also, immune response to enzyme replacement therapy proteins has been reported and can have adverse effects and alter the safety and efficacy of ERT (Brooks D A (1999) Molec Genet Metab 68(2):268-275).

TABLE 1

Enzyme Replacement Therapy (ERT) for Lysosomal Storage Diseases (LSD)

| Disease | Enzyme replaced | Company | Status |
|---|---|---|---|
| Gaucher, type 1 and type 3 | Glucocerebrosidase | Genzyme | approved EU/US (1991) |
| Fabry | α-galactosidase A | Genzyme Transkaryotic Therapies | approved EU (2001) approved US (2003) approved EU (2001) |
| MPS I (Hurler) | α-L-iduronidase | BioMarin Pharmaceutical/Genzyme | approved EU/US (2003) |
| MPS IV (Maroteaux-Lamy) | arylsulfatase B | BioMarin Pharmaceutical | approved US (2005) |
| Pompe | α-glucosidase | Genzyme | phase III clinical trial |
| MPS II (Hunter) | α-L-iduronate sulfatase | Transkaryotic Therapies | phase III clinical trial |
| Niemann-Pick B | acid sphingomylinase | Genzyme | pre-clinical |
| Metachromatic leukodystrophy | arylsulfatase A | Zymenex | pre-clinical |
| α-Mannosidosis | 1183α-mannosidase | Zymenex | pre-clinical |

TABLE 2

Therapies including ERT in Gaucher Diseases

| Agent | Mechanism | Manufacturer | Status |
|---|---|---|---|
| Imiglucerase (ERT) | Rh GBA1 | Genzyme Corporation | FDA approved |
| Velaglucerase alfa (ERT) | Rh GBA1 | Shire plc | FDA approved |
| Taliglucerase alpha (ERT) | Plant-derived GBA1 | Protalix and Pfizer | FDA approved |
| Miglusta (SRT) | Inhibits glucosylceramide synthase | Actelion | Under development |
| Isofagomine tartrate (PCT) | Chaperoning, facilitates GBA folding and trafficking | Amicus Therapeutics | Under development |

Therefore, in view of the aforementioned deficiencies attendant with prior art methods of evaluating, ameliorating and treating lysosomal storage diseases, including Gaucher's Disease, it should be apparent that there still exists a need in the art for alternative therapies, additional agents, and improved and more correlative diagnostics for lysosomal storage diseases, including Gaucher's Disease. The present invention provides novel activity, use and application of one or more progranulin (PGRN) derivative or fragment, including in amelioration, and treatment of lysosomal storage diseases, including Gaucher's Disease.

The citation of references herein shall not be construed as an admission that such is prior art to the present invention.

SUMMARY OF THE INVENTION

The present invention provides and relates to particular and unique derivatives or fragments of progranulin PGRN. In a particular aspect, the PGRN derivatives bind glucocerebrosidase (GBA) and facilitate delivery of GBA to the lysosome. In an aspect, the invention provides PGRN derivative ND7/Pcgin and corresponding amino acids 496-593 of human PGRN. In an aspect of the invention, the PGRN fragment or derivative is a fragment of full length PGRN and comprises amino acids 496-593 of human PGRN. In an aspect of the invention, the PGRN fragment or derivative is a fragment of full length PGRN and consists of amino acids 496-593 of human PGRN.

It has been recently discovered that mutations in the gene encoding progranulin (PGRN), including the absence of PGRN by gene knockout, lead to Gaucher's disease, a genetic disease previously known to be only caused by or associated with glycocerebrosidase enzyme gene (GBA1) mutations. PGRN knockout (KO) (null mutant) mice develop Gaucher's disease, including the classical pathological appearance of Gaucher cells, which is diagnostic of lysosome storage disorders under the electronic microscope. Lipid analysis of PGRN KO mice shows glycocerebrosidase enzyme substrate glucosylceramide, denoted β-GlcCer, accumulation in macrophages.

Studies demonstrating that PGRN binds glycocerebrosidase (GBA) and the delivery of the GBA1 enzyme to the lysosome is impaired in PGRN KO mice are described in PCT/US2015/014364 filed Feb. 4, 2015 and U.S. 61/935,541 filed Feb. 4, 2014, incorporated herein by reference. Imuglucerase, a clinical drug used to treat Gaucher's disease, rescues the Gaucher's disease phenotype in PGRN KO mice.

In an aspect of the invention, an effective PGRN fragment or derivative is provided wherein the fragment or derivative is not full length or wild type PGRN. The effective PGRN polypeptide of the invention represents a portion, part or fragment of full length PGRN, wherein said portion, part or fragment is effective in binding GBA/GCase. In an aspect the effective PGRN fragment or derivative of the invention, distinct from full length PGRN, is capable of binding GBA and facilitating lysosomal delivery thereof. In an aspect, the effective PGRN fragment or derivative of the invention, distinct from full length or wild type PGRN, lacks oncogenic activity of full length PGRN.

The present invention provides a derivative of PGRN, corresponding to amino acids 496-593 of human PGRN, denoted ND7/Pcgin, which is active and effective in binding GBA and facilitating lysosomal delivery in lieu of full length PGRN. The derivative of PGRN of the invention represents and is a fragment of PGRN comprising a portion of PGRN which is not full length PGRN and is distinct from wild type PGRN in amino acid sequence, wherein the derivative is a part or portion of PGRN that is effective in binding GBA/GCase. In an aspect, the derivative of PGRN of the invention represents and is a fragment of PGRN consisting of a portion of PGRN which is not full length PGRN and is distinct from wild type PGRN in amino acid sequence, consisting of a part or portion of PGRN that is effective in binding GBA/GCase.

In an aspect, the invention relates to a fragment or derivative of PGRN comprising a portion of PGRN which is not full length PGRN and is distinct from wild type PGRN in amino acid sequence capable of binding or complexing with lysosomal enzymes such as sortilin and/or HSP70. ND7/Pcgin, including active variants thereof, provides a novel alternative to PGRN (particularly full length or wild type PGRN) and to PGRN peptide atsttrin, particularly a smaller active peptide molecule, for use and application in lysosomal trafficking, and in lysosomal storage disease(s), including Gaucher's disease.

In an aspect, the PGRN derivatives or fragments of the invention have amino acid sequence corresponding to ND7/Pcgin and human PGRN amino acids 496-593. In an aspect, the the PGRN derivatives or fragments of the invention have amino acid sequence corresponding to ND7/Pcgin and human PGRN amino acids 496-593, wherein at least one amino acid is substituted. In an aspect, the the PGRN derivatives or fragments of the invention have amino acid sequence corresponding to ND7/Pcgin and human PGRN amino acids 496-593, wherein one or more amino acid is substituted. In an aspect, the the PGRN derivatives or fragments of the invention have amino acid sequence corresponding to ND7/Pcgin and human PGRN amino acids 496-593, wherein at least one, at least two, at least three, at least four, at least five, at least one and not more than five, at least one and no more than ten, amino acid(s) is substituted. In an aspect, one or more ND7 human PGRN amino acid selected from amino acids 496-593 is substituted with the corresponding amino acid from mouse PGRN sequence, including as depicted in and selected from FIG. 10.

Active variants of ND7/Pcgin are contemplated by the present invention, including wherein one or more amino acid in human PGRN amino acids 496-593 are substituted. In an aspect, the PGRN derivative of the invention is a sequence corresponding to amino acids 496-593 of human PGRN wherein one amino acid is substituted and the sequence is distinct from human PGRN amino acids 496-593, including distinct from the sequence of FIG. 8C and SEQ ID NO: 4 by at least one amino acid.

The invention provides PGRN derivative ND7/Pcgin, particularly amino acids corresponding to human PGRN 496-593, including variants having at least one or more amino acid substitutions in human PGRN sequence, as modulators of lysosomal storage disease and of lysosomal trafficking. In particular, the invention provides PGRN derivative ND7/Pcgin as a novel facilitator of lysosomal enzyme trafficking to the lysosome. In a particular embodiment, the present invention relates to ND7/Pcgin sequence and all variants thereof which are capable of facilitating enzyme delivery to the lysosome, and/or binding or complexing with lysosomal enzymes such as glycocerebrosidase (GBA). In an aspect, the invention relates to ND7 sequence and all variants thereof which are capable of binding or complexing with lysosomal enzymes such as sortilin and/or HSP70.

In an aspect, the the PGRN derivatives or fragments of the invention have amino acid sequence corresponding to ND7/Pcgin or to SEQ ID NO:4 or variants thereof having at least 80% amino acid identity to SEQ ID NO:4, wherein said variants bind GBA/GCase. In an aspect, the the PGRN derivatives or fragments of the invention have amino acid sequence corresponding to ND7/Pcgin or to SEQ ID NO:4 or variants thereof having at least 80% amino acid identity to SEQ ID NO:4, wherein said variants bind one or more of GBA, HSP70 and sortilin.

In an aspect, the the PGRN derivatives or fragments of the invention have amino acid sequence corresponding to ND7/Pcgin or to SEQ ID NO:4 or variants thereof having at least 85% amino acid identity to SEQ ID NO:4, wherein said variants bind GBA/GCase. In an aspect, the the PGRN derivatives or fragments of the invention have amino acid sequence corresponding to ND7/Pcgin or to SEQ ID NO:4 or variants thereof having at least 85% amino acid identity to SEQ ID NO:4, wherein said variants bind one or more of GBA, HSP70 and sortilin.

In an aspect, the the PGRN derivatives or fragments of the invention have amino acid sequence corresponding to ND7/Pcgin or to SEQ ID NO:4 or variants thereof having at least 90% amino acid identity to SEQ ID NO:4, wherein said variants bind GBA/GCase. In an aspect, the the PGRN derivatives or fragments of the invention have amino acid sequence corresponding to ND7/Pcgin or to SEQ ID NO:4 or variants thereof having at least 90% amino acid identity to SEQ ID NO:4, wherein said variants bind one or more of GBA, HSP70 and sortilin.

It is an object of the present invention to provide pharmaceutical compositions for use in therapeutic methods which comprise or are based upon the PGRN peptide ND7/Pcgin as described herein. It is an object of the present invention to provide pharmaceutical compositions for use in therapeutic methods which comprise or are based upon PGRN ND7/Pcgin, including comprising the peptide sequences set out in FIG. 8C, particularly comprising or consisting of SEQ ID NO: 4. The pharmaceutical compositions include combinations of one or more PGRN ND7/Pcgin peptide, including variants thereof, which are capable of facilitating enzyme delivery to the lysosome, and/or binding or complexing with lysosomal enzymes such as glycocerebrosidase (GBA/GCase), or with sortilin and/or HSP70, and/or capable of reducing lysosomal substrate accumulation, such as β-GlcCer, in the lysosome or macrophage.

The pharmaceutical compositions include combinations of PGRN ND7/Pcgin fragment or variant(s) thereof having activity as provided herein and one or more lysosomal enzyme or lysosomal substrate reducing agent. Lysosomal enzymes or lysosomal substrate reducing agents include and may be selected from one or more of glucocerebrosidase, α-galactosidase, β-galactosidase, β-hexosaminidase and sphingomyelinase. The pharmaceutical compositions include combinations of ND7/Pcgin or variants thereof having GBA binding activity and one or more of Imiglucerase, Velaglucerase alfa, Taliglucerase alpha, Miglusta and Isofagomine tartrate.

Thus, the invention provides a composition for treatment or alleviation of a lysosomal storage disease comprising isolated PGRN ND7/Pcgin, or active variants thereof, wherein said PGRN ND7/Pcgin has an amino acid sequence as set out in FIG. 8C or in SEQ ID NO: 4, including an amino acid sequence wherein one or more amino acid is substituted, including substitution with one or more corresponding mouse PGRN amino acid sequence. The composition may further comprising an enzyme replacement therapy agent or substrate reduction therapy agent for a lysosomal storage disease, including one or more of glucocerebrosidase, α-galactosidase, β-galactosidase, β-hexosaminidase and sphingomyelinase. In one such aspect, the invention provides a composition comprising PGRN ND7/Pcgin, or active variant thereof, in combination with glucocerebrosidase for treatment or alleviation of Gaucher's Disease. In an aspect, compositions of the invention may further comprise one or more molecular chaperone or lysosomal delivery protein, including HSP70 and/or sortilin. Compositions of the invention include pharmaceutical compositions further comprising a pharmaceutically acceptable carrier, vehicle, diluent or excipient.

In a further embodiment, the present invention relates to certain therapeutic methods which would be based upon the activity of PGRN ND7/Pcgin, or active variants thereof, in facilitating enzyme delivery to the lysosome, and/or binding or complexing with lysosomal enzymes such as glycocerebrosidase (GBA), or with sortilin and/or HSP70, and/or being capable of reducing lysosomal substrate accumulation, such as β-GlcCer, in the lysosome or macrophage.

Thus, the present invention provides methods for facilitating lysosomal delivery of a protein or enzyme in an animal comprising administering to said animal isolated PGRN ND7/Pcgin, or active variants thereof. In an aspect thereof said PGRN ND7/Pcgin or active variant comprises an amino acid sequence as set out in FIG. 8C or SEQ ID NO: 4, including wherein one or more amino acid is substituted, including wherein at least one amino acid sequence is substituted. In an aspect of the invention, a method is provided for facilitating delivery of glycocerebrisidase (GBA) in a patient with Gaucher's Disease comprising administering to said patient isolated PGRN ND7/Pcgin, or active variants thereof including atsttrin, wherein said PGRN ND7/Pcgin has an amino acid sequence as set out in FIG. 8C, including wherein at least one amino acid is substituted, wherein one or more amino acid is substituted, including an amino acid substitution as depicted in FIG. 19.

The invention provides methods for treating or alleviating a lysosomal storage disease in an animal comprising administering to said animal isolated PGRN derivative ND7/Pcgin or an active variant thereof, including wherein said PGRN ND7/Pcgin has an amino acid sequence as set out in FIG. 8C or SEQ ID NO:4, including wherein at least one amino acid is substituted, wherein one or more amino acid is substituted. In an aspect of these methods, the method comprises additionally administering one or more lysosomal enzyme which is reduced, absent, mutated or altered in the lysosomal storage disease. The lysosomal enzyme may be selected from one or more of a glucocerebrosidase, α-galactosidase, β-galactosidase, β-hexosaminidase and sphingomyelinase.

The lysosomal storage disease of the methods of the invention may be selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. In an aspect, the lysosomal storage disease of the methods of the invention may be selected from Gaucher's disease (GD), Tay-sachs disease (TSD), mucolipidosis (ML), mucopolysaccharidosis (MPS), metachromatic leukodystrophy (MLD), Farber disease (FD) and Krabbe disease (KD). In one aspect, the lysosomal storage disease of the methods of the invention may be selected from Gaucher's disease (GD) including GD Type I, II or III, Tay-Sachs disease (TSD), mucolipidosis (ML) including ML III, mucopolysaccharidosis (MPS) including MPS II, III, VI, metachromatic leukodystrophy (MLD), Farber disease (FD) and Krabbe disease (KD). In a particular preferred aspect of the methods of the invention, the lysosomal storage disease (LSD) is Gaucher's Disease (GD). In an aspect of the methods of the invention, the method comprise additionally administering the lysosomal enzyme glycocerebrisidase (GBA) or an active fragment or recombinant form thereof for treating or alleviating Gaucher's Disease. In a particular preferred aspect of the methods of the invention, the lysosomal storage disease (LSD) is Tay-Sachs disease.

Other objects and advantages will become apparent to those skilled in the art from a review of the following description which proceeds with reference to the following illustrative drawings.

BRIEF DESCRIPTION OF THE DRAWINGS

FIG. 5 depicts expression of PGRN serial deletions from the C-terminal end. (A) Scheme of constructs encoding serial GFP-tagged C-terminal deletion mutants of PGRN. PGRN full-length (aa 1-593), CD1 (aa 1-521), CD2 (aa 1-444), CD3 (aa 1-376), CD4 (aa 1-284), CD5 (aa 1-209), CD6 (aa 1-127), and CD7 (aa 1-61). (B) Expression of GFP-tagged C-terminal deletion PGRN fragments, examined by immunoblotting with anti-GFP antibody.

FIG. 18 depicts the amino acid sequence of (A) human PGRN (SEQ ID NO: 2) and (B) mouse PGRN (SEQ ID NO: 3).

FIG. 19 provides an aligned comparison of the human PGRN ND7/Pcgin (amino acids 496-593) with corresponding mouse amino acids (SEQ ID NO: 6). Amino acid differences are denoted with a dot. Gaps for sequence alignment are shown as dashes -.

DETAILED DESCRIPTION

Figure 1:
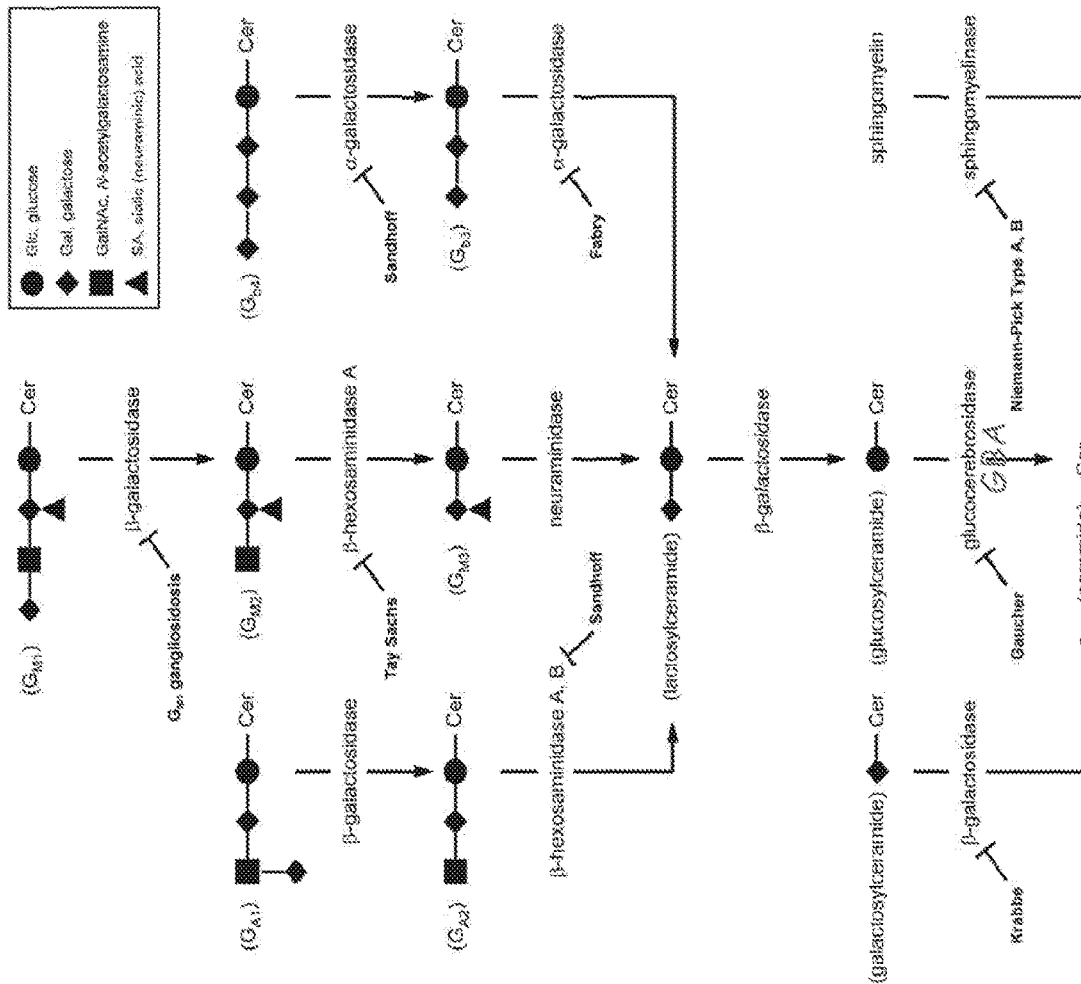
FIG. 1 depicts pathways for glycosphingolipids implicated in lysosomal storage diseases (LSD). Glycosphingolipid metabolism is a process mediated by multiple enzymes. Enzyme insufficiency causes accumulation of the corresponding substrate in lysosomes. Gaucher's disease, the most common LSD, is caused by mutation of glucocerebrosidase (GBA). Mutation of GBA leads to the accumulation of the GBA substrate, β-glucosylceramide β-GlcCer), in macrophages.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "progranulin", "PGRN", "granulin-epithelin precursor", "GEP", "PC-cell-derived growth factor", "PCDGF", "proepithelin", "acrogranin", and "GP80" may be used herein interchangeably, and extends to those proteins, particularly the full length PGRN proteins, including human and mouse PGRN, particularly human PGRN. Human and mouse full length PGRN have the amino acid sequence data described herein and presented in FIGS. 18A and 18B, including as set out in SEQ ID NO: 2 and SEQ ID NO: 3, respectively.

The terms "granulin(s)", "epithelins" or any of "Granulins A-E", "GrnA", "GrnB", "GrnC", "GrnD", "GrnE" refer to particular cysteine rich motifs, of approximately 6 kDa in size, comprising or having the sequence motif $CX_{5-6}CX_5CCX_8CCX_6CCXDX_2HCCPX_4CX_{5-6}C$ (SEQ ID NO: 1), which granulins may be released by proteolytic processing from the GEP polypeptide molecule.

Atsttrin is a PGRN-derived engineered protein (Antagonist of TNF/TNFR Signaling via Targeting TNF Receptors), comprising combinations of half units of PGRN units A, C and F in combination with linker units P3, P4 and P5 (U.S. Pat. No. 8,362,218; WO 2010120374). U.S. Pat. No. 8,362,218 and PCT publication WO 2010120374 describe PGRN-derived peptides comprising a combination of half units of progranin/granulin units, wherein at least one half unit is ½ F, and linker units, particularly at least two linker units. The amino acid sequence of atsttrin is:

Atsttrin peptide sequence (½F+P3+P4+½A+P5+½C): PQASCCEDRVHCCPHGAFCDLVHTRCITPTGTH-PLAKKLPAQRTNRAVALSSSASSKEN ATTDLLTKLPAHTVGDVKCDMEVSCPDGYTC-CRLQSGAWPWCEQGPHQVPWMEKAP AHL-SLPDPQALKRDVPCDNVSSCPSSDTCCQLT-SGEWGCCPIP (SEQ ID NO: 5).

The terms "PGRN ND7 fragment", "PGRN ND7 derivative", "ND7", "aa496-593", "PGRN C-terminus for GCase Interaction" and "Pcgin" refer to peptides, including single or multiple proteins, refer to derivatives or fragments derived from PGRN, and extends to those proteins having the amino acid sequence data described herein and presented in FIG. 8C and as set out in SEQ ID NO: 4, and the profile of activities and capabilities described and set forth herein and provided in the Claims. ND7/Pcgin may have the sequence corresponding to amino acids 496-593 of human PGRN. Active ND7 PGRN/Pcgin peptides having activity in facilitating enzyme delivery to the lysosome, and/or binding or complexing with lysosomal enzymes such as glycocerebrosidase (GBA), are included and provided herein. These active ND7 PGRN/Pcgin peptides may retain biological activity and be active in activity assays, including in cell growth assays, enzyme substrate accumulation assays, protein binding including GBA(GCase), and/or sortilin and/or HSP70 binding, GBA/GCase and/or other lysosomal enzyme processing or delivery to the lysosome, and assessment for Gaucher type cells. ND7 and Pcgin includes variants, and derivatives of the peptides, and may include active fragments of ND7/Pcgin. Accordingly, proteins displaying substantially equivalent activity, and which are modifications thereof, are likewise contemplated. These modifications may be deliberate, for example, such as modifications obtained through site-directed mutagenesis, or may be accidental, such as those obtained through mutations in hosts that are producers of the complex or its named subunits. The terms "PGRN ND7 fragment", "PGRN ND7 derivative", "ND7", "aa496-593", "PGRN C-terminus for GCase Interaction" and "Pcgin" are intended to include within their scope proteins specifically recited herein as well as all substantially homologous analogs and allelic variations.

Corresponding mouse or other species or ortholog PGRN sequences to the human ND7/Pcgin sequence are further contemplated. Variants of ND7/Pcgin having at least one amino acid sequence substitution in amino acids 496-593 of human PGRN are contemplated. Variants of ND7/Pcgin having more than one amino acid sequence substitution in amino acids 496-593 of human PGRN are contemplated. Variants of ND7/Pcgin having at least two amino acid sequence substitutions in amino acids 496-593 of human PGRN are contemplated. Variants of ND7/Pcgin having at least three amino acid sequence substitutions in amino acids 496-593 of human PGRN are contemplated. Variants of ND7/Pcgin having at a few or several substitutions, up to three substitutions, up to four substitutions, up to five substitutions, up to six substitutions, in amino acids 496-593 of human PGRN are contemplated. Variants may include wherein one or more amino acid(s) in the human ND7/Pcgin sequence of amino acids 496-593 of human PGRN are replaced with one or more corresponding mouse amino acid, including as depicted in FIG. 19. Variants may include wherein one or more amino acid(s) in the human ND7/Pcgin sequence of amino acids 496-593 of human PGRN are replaced with one or more corresponding mouse amino acid or an amino acid conserved with the corresponding mouse amino acid (such as an Ile or Val conserved for a Leu mouse amino acid, a Lys conserved for an Arg mouse amino acid, etc.). Mouse PGRN sequences corresponding to human ND7/Pcgin amino acids 496-593 (SEQ ID NO: 6) are depicted in FIG. 19 wherein human and mouse sequence are compared and aligned. Mouse amino acids which may be suitable for substitution in the human ND7/Pcgin sequence are shown in FIG. 19, such as for example those indicated by a dot. Also, conservative substitutions based on mouse amino acids suitable for substitution are evident from a review of the sequence comparison in FIG. 19.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |

-continued

| TABLE OF CORRESPONDENCE | | |
|---|---|---|
| SYMBOL | | |
| 1-Letter | 3-Letter | AMINO ACID |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding the PGRN fragment or derivative, which code for a peptide having the same amino acid sequence as PGRN peptide ND7/Pcgin, or encode amino acids 496-593 or an active fragment thereof, including as set out in FIG. 8C and in SEQ ID NO:4, including wherein an amino acid, or one or more amino acid is substituted, but which are degenerate to any such sequences. By "degenerate to" is meant that a different three-letter codon is used to specify a particular amino acid. It is well known in the art that the following codons can be used interchangeably to code for each specific amino acid:

Phenylalanine (Phe or F) UUU or UUC
Leucine (Leu or L) UUA or UUG or CUU or CUC or CUA or CUG
Isoleucine (Ile or I) AUU or AUC or AUA
Methionine (Met or M) AUG
Valine (Val or V) GUU or GUC of GUA or GUG
Serine (Ser or S) UCU or UCC or UCA or UCG or AGU or AGC
Proline (Pro or P) CCU or CCC or CCA or CCG
Threonine (Thr or T) ACU or ACC or ACA or ACG
Alanine (Ala or A) GCU or GCG or GCA or GCG
Tyrosine (Tyr or Y) UAU or UAC
Histidine (His or H) CAU or CAC
Glutamine (Gln or Q) CAA or CAG
Asparagine (Asn or N) AAU or AAC
Lysine (Lys or K) AAA or AAG
Aspartic Acid (Asp or D) GAU or GAC
Glutamic Acid (Glu or E) GAA or GAG
Cysteine (Cys or C) UGU or UGC
Arginine (Arg or R) CGU or CGC or CGA or CGG or AGA or AGG
Glycine (Gly or G) GGU or GGC or GGA or GGG
Tryptophan (Trp or W) UGG
Termination codon UAA (ochre) or UAG (amber) or UGA (opal)

It should be understood that the codons specified above are for RNA sequences. The corresponding codons for DNA have a T substituted for U.

Mutations can be made in the PGRN derivative or fragment, particularly in amino acids of ND7/Pcgin peptide, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids, based on their R groups: Amino acids with nonpolar R groups: Alanine, Valine, Leucine, Isoleucine, Proline, Phenylalanine, Tryptophan, Methionine; Amino acids with uncharged polar R groups: Glycine, Serine, Threonine, Cysteine, Tyrosine, Asparagine, Glutamine; Amino acids with charged polar R groups (negatively charged at Ph 6.0): Aspartic acid, Glutamic acid; Basic amino acids (positively charged at pH 6.0): Lysine, Arginine, Histidine (at pH 6.0). Another grouping may be those amino acids with phenyl groups: Phenylalanine, Tryptophan, and Tyrosine. Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly Preferred Substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

As used herein, "pg" means picogram, "ng" means nanogram, "ug" or "μg" mean microgram, "mg" means milligram, "ul" or "μl" mean microliter, "ml" means milliliter, "l" means liter.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules are prepared by the proteolytic reaction of papain and pepsin, respectively, on substantially intact antibody molecules by methods that are well-known. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The term "therapeutically effective amount" means that amount of a drug, compound, peptide, or pharmaceutical agent that will elicit the biological, physiological, clinical, or medical response of a subject that is being sought by a medical doctor or other clinician. The phrase "therapeutically effective amount" is used herein to include an amount sufficient to prevent, and preferably reduce by at least about 30 percent, more preferably by at least 50 percent, most preferably by at least 90 percent, a clinically significant change in the S phase activity of a target cellular mass, in the enlargement of an organ, in the accumulation of a substrate or protein, in a neurological deficit or impairment, or other feature of pathology such as for example, elevated blood pressure, fever or white cell count, enlargement of the spleen or liver as may attend its presence and activity.

The term "preventing" or "prevention" refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term "prophylaxis" is related to and encompassed in the term "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease. In an aspect, the term "alleviate" or "alleviation" refers to and includes the reduction in the manifestation, extent or severity of a disease or symptom(s) thereof, recognizing that such reduction can serve to reduce pain, suffering, physical or physiological deficit(s), and improve clinical parameters associated with a disease, while not curing or fully eliminating said disease.

The term "lysosomal storage disease(s)", "LSD" refers to a heterogeneous group of diseases or disorders characterized by the accumulation of undigested or partially digested macromolecules, which ultimately results in cellular dysfunction and clinical abnormalities. LSDs result from gene mutations in one or more of lysosomal enzymes, resulting in accumulation of the enzyme substrates in lysosomes, ultimately leading in many instances to organomegaly, connective-tissue and ocular pathology, and central nervous system dysfunction. Lysosomal storage disease(s) include sphingolipidoses, gangliosidosis, mucopolysaccharidoses, glycoprotein storage diseases, mucolipidoses. The term includes, but is not limited to, exemplary diseases selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. In a particular aspect a preferred lysosomal storage disease is Gaucher's Disease, including Type I, Type II and/or Type III Gaucher's Disease.

The term "Gaucher's Disease", "GD", refers to the most common of the lysosomal storage diseases, Gaucher's Disease. Gaucher's disease involves dysfunctional metabolism of sphingolipids and classically results from hereditary deficiency of the enzyme glucocerebrosidase (GBA/GCase).

It has been previously demonstrated, particularly by the present inventors, that the protein Progranulin PGRN plays an important and critical role in the transport of lysosomal enzymes to the lysosome. As such, PGRN, and PGRN-derived active peptide atsttrin, have a therapeutic, prophylactic, and diagnostic use and application in lysosomal storage diseases and disorders. PCT/US2015/014364 filed Feb. 4, 2015 and provisional application 61/935,541 filed Feb. 4, 2014, incorporated herein by reference in their entirety, demonstrate PGRN binding to lysosomal enzymes, including particularly to galactocerebrosidase (GBA). PGRN and particularly PGRN/lysosomal enzyme complexes, such as PGRN/GBA complexes, bind to lysosomal/endosomal trafficking and sorting proteins, including sortilin and HSP70. Lysosomal storage disease, including Gaucher's disease, develops in the absence of PGRN or with mutated PGRN, such as in PGRN knockout (KO) animals. Over 70% of GD patients also have mutations in PGRN. Thus, PGRN and PGRN peptide atsttrin, are applicable for diagnosis, amelioration and therapy in lysosomal storage disease(s), including Gaucher's Disease.

The present invention provides a novel and unique derivative of PGRN, fragment derivative denoted ND7/Pcgin, corresponding to amino acids 496-593 of human PGRN, and the invention includes use and applications of the PGRN peptide derivative or fragment ND7/Pcgin and active variants thereof in the prevention, treatment or alleviation of lysosomal storage disease or disorders (LSD), particularly Gaucher's disease. The PGRN fragment or derivatives of the invention bind to GBA and enable PGRN trafficking to the lysosome in lysosomal storage disease cells. The PGRN fragment or derivatives of the invention are distinct from full length PGRN or wild type PGRN and represent a portion of full length PGRN. The invention includes use and applications of the PGRN fragment(s) or derivative(s), particularly ND7/Pcgin, for prevention, treatment or alleviation of lysosomal storage diseases, including conditions, symptoms and clinical manifestations of accumulation of substrates and/or molecules in lysosomes.

The invention provides an active fragment or portion of full length PGRN, wherein the fragment comprises amino acids 496-593 of human PGRN, and the invention includes use and applications of the PGRN peptide derivative or fragment ND7/Pcgin, including active fragments of ND7, in the prevention, treatment or alleviation of lysosomal storage disease or disorders (LSD), particularly Gaucher's disease. Thus, larger fragments of PGRN than ND7/Pcgin and amino acids 496-593 are contemplated. The larger fragments may include additional PGRN amino acids, nonetheless said larger fragments are active fragments and/or portions of full length PGRN and are distinct from full length PGRN, lacking amino acids of native full length PGRN. Similarly, smaller fragments of PGRN than ND7/Pcgin and amino acids 496-593, particularly active fragments thereof, are also contemplated. In an aspect, an active fragment or portion of ND7/Pcgin includes wherein portions and internal amino acids among 496-593 are deleted.

Lysosomal storage diseases include sphingolipidoses, gangliosidosis, mucopolysaccharidoses, glycoprotein storage diseases, mucolipidoses and exemplary diseases selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. Lysosomal storage diseases include disease(s) wherein trafficking of GBA to the lysosome is altered, particularly including Gaucher's disease. The invention includes use and applications of the PGRN fragment and derivative of the invention for prevention, treatment or alleviation of and/or for specific therapeutic intervention of lysosomal storage disorders by facilitating delivering of required or relevant lysosomal agents, enzymes and/or other molecules to the lysosome.

The possibilities both diagnostic and therapeutic that are raised by the existence of lysosomal protein/enzyme binding peptides, particularly the PGRN fragment or derivative of the present invention, as described herein, derive from the fact that the ND7/Pcgin fragment participates in protein-protein interaction with lysosomal protein(s)/enzyme(s), such as glucocerebrosidase (GBA), and may serve to initiate, facilitate, mediate the transport and/or trafficking of lysosomal protein(s)/enzyme(s), such as glucocerebrosidase (GBA), to the lysosome where they are required for activity to maintain the lysosomal compartment and overall proper and effective protein trafficking and degradation. Thus, the present invention contemplates ND7/Pcgin-mediated pharmaceutical intervention in the trafficking and delivery of required enzymes/proteins in and to the lysosome and proper lysosomal function to modulate, alleviate, prevent or treat lysosomal storage diseases or disorders and any other conditions which are associated with altered or insufficient trafficking of proteins and enzymes to the lysosome or endosome.

The invention provides PGRN peptides, particularly the ND7/Pcgin PGRN fragment or derivative provided herein and variants thereof, as modulators of lysosomal storage disease and of lysosomal trafficking. In a particular embodiment, the present invention relates to and includes derivatives of PGRN having amino acids 496-593 of PGRN or variants thereof which are capable of facilitating enzyme delivery to the lysosome, and/or binding or complexing with lysosomal enzymes such as glycocerebrosidase (GBA), or with sortilin and/or HSP70. In a further particular aspect PGRN derivative ND7/Pcgin has the amino acid sequence set out in FIG. 8C and SEQ ID NO: 4 and amino acids 496-593 of human PGRN.

It is an object of the present invention to provide pharmaceutical compositions for use in therapeutic methods which comprise or are based upon the PGRN fragment or derivatives of the invention. The pharmaceutical compositions include combinations of one or more PGRN fragments or derivatives which are capable of facilitating enzyme delivery to the lysosome, and/or binding or complexing with lysosomal enzymes such as glycocerebrosidase (GBA), or with sortilin and/or HSP70, and/or capable of reducing lysosomal substrate accumulation, such as β-GlcCer, in the lysosome or macrophage. The pharmaceutical compositions include combinations of the PGRN fragment or derivatives, particularly ND7/Pcgin or active variants thereof, and one or more lysosomal enzyme or lysosomal substrate reducing agent. Lysosomal enzymes or lysosomal substrate reducing agents include and may be selected from one or more of glucocerebrosidase, α-galactosidase, β-galactosidase, β-hexosaminidase and sphingomyelinase. The pharmaceutical compositions include combinations of the PGRN fragment or derivatives, particularly ND7/Pcgin or active variants thereof, and one or more of Imiglucerase, Velaglucerase alfa, Taliglucerase alpha, Miglusta and Isofagomine tartrate.

Figure 8:
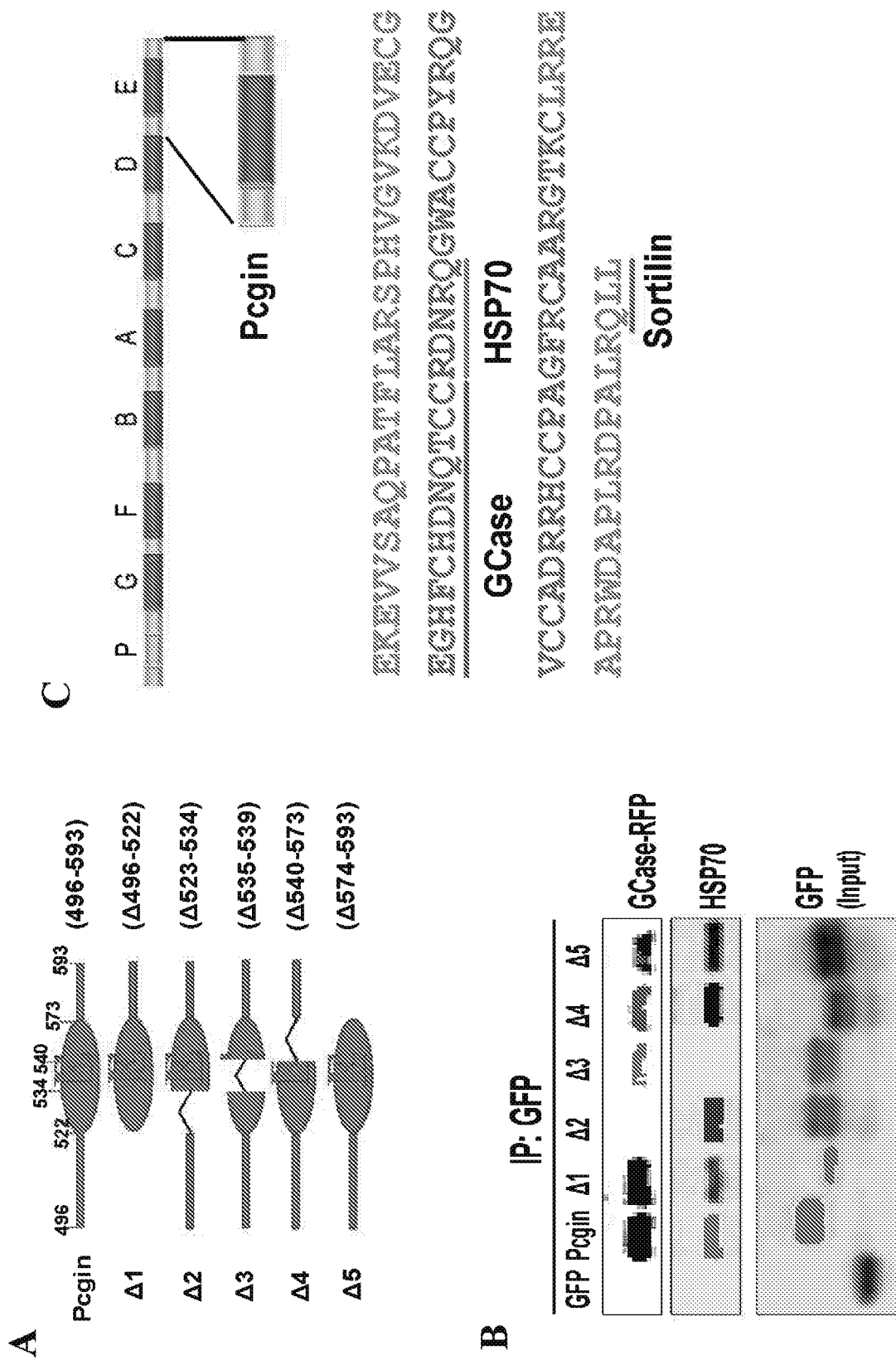
FIG. 8 depicts that Pcgin/ND7 fragment of PGRN has binding motifs for GCase and HSP70. (A) Scheme of Pcgin amino acid structure and its deletion mutants. (B) Co-IP assays for examining the binding of Pcgin and its mutants to GCase and HSP70. 293T cells were transfected with plasmids encoding either GFP fused Pcgin or its mutants, together with plasmids encoding RFP fused GCase and HSP70, and the protein complexes were immunoprecipitated with GFP antibody and probed with RFP or HSP70 antibodies respectively. Bottom panel shows the expressions of Pcgin and its mutants in the transfected cells. The result is representative of three independent experiments. (C) Structure and sequence of Pcgin/ND7 fragment of PGRN. Pcgin is derived from C-terminal human PGRN from aa496-593, containing Grn E and linker regions on both sides (top panel). Sequence of Pcgin (SEQ ID NO:4) is shown in the bottom panel. Linker regions and Grn E are highlighted in green and red, respectively. Binding sites of GCase (EGHFCHDNQTCC (SEQ ID NO:7), HSP70 (RDNRQ (SEQ ID NO:8), and Sortilin are indicated.

Thus, the invention provides a composition for treatment or alleviation of a lysosomal storage disease comprising isolated PGRN derivative ND7/Pcgin or active variants thereof, wherein said PGRN derivative or active variant comprises or consists of the amino acid sequence as set out in FIG. 8 and in SEQ ID NO: 4. In an aspect, the invention provides a composition for treatment or alleviation of a lysosomal storage disease comprising isolated PGRN derivative ND7/Pcgin or a PGRN peptide of amino acids 496-593 or a variant thereof wherein said PGRN variant comprises an amino acid sequence having at least one amino acid substitution, deletion or addition in comparison to the sequence as set out in FIG. 8C and in SEQ ID NO: 4. Thus, in one aspect the PGRN derivative of use in the invention has at least one amino acid difference versus the corresponding sequence region in wild type or natural human PGRN. Thus in an aspect of the invention, the PGRN derivative of the invention comprises or consists of a fragment or portion of PGRN corresponding to amino acids 496-593 of human PGRN, wherein at least one amino acid or wherein one or more amino acid is substituted or changed versus wild type or natural human PGRN, and wherein the derivative binds GBA/GCase, facilitates GBA transport, and/or alleviates accumulation of GBA in lysosomes in lysosomal storage disease. In one such aspect, compositions are provided comprising the PGRN derivative ND7/Pcgin or variants thereof having at least one amino acid substitution or change versus wild type human PGRN in combination with glucocerebrosidase for treatment or alleviation of Gaucher's Disease.

In an aspect, the PGRN derivative of the invention comprises or consists of a fragment or portion of PGRN corresponding to amino acids 496-593 of human PGRN, wherein at least one amino acid, or wherein one or more amino acid is substituted or changed versus wild type or natural human PGRN, wherein the at least one or one or more amino acid substitution is a substitution with the corresponding mouse PGRN amino acid, or an amino acid conserved with the corresponding mouse PGRN amino acid, including as selected from an amino acid depicted in FIG. 19, and wherein the derivative binds GBA/GCase, facilitates GBA transport, and/or alleviates accumulation of GBA in lysosomes in lysosomal storage disease.

In an aspect, compositions of the invention may further comprise one or more molecular chaperone or lysosomal delivery protein, including HSP70 and/or sortilin.

In an aspect of the invention, a variant of ND7/Pcgin and of amino acids 496-593 of human PGRN is contemplated wherein said variant has at least 80% amino acid sequence identity to ND7/Pcgin or amino acids 496-593 of human PGRN, at least 85% amino acid sequence identity to ND7/Pcgin or amino acids 496-593 of human PGRN, at least 90% amino acid sequence identity to ND7/Pcgin or amino acids 496-593 of human PGRN, at least 95% amino acid sequence identity to ND7/Pcgin or amino acids 496-593 of human PGRN, at least 98% amino acid sequence identity to ND7/Pcgin or amino acids 496-593 of human PGRN, at least 99% amino acid sequence identity to ND7/Pcgin or amino acids 496-593 of human PGRN. In each instance at least one amino acid differs from the corresponding amino acid sequence in human PGRN for amino acids 496-593. Thus at least one amino acid sequence is different from the sequence provided in FIG. 8C and SEQ ID NO: 4. In an aspect, at least one amino acid sequence is different from the sequence provided in FIG. 8C and SEQ ID NO: 4, and is replaced with a corresponding mouse amino acid as selected from those depicted and provided in FIG. 19.

Compositions of the invention include pharmaceutical compositions further comprising a pharmaceutically acceptable carrier, vehicle, diluent or excipient. The PGRN fragment and derivative described herein, particularly including ND7/Pcgin, or an active variant thereof, may be prepared in pharmaceutical compositions, with a suitable carrier and at a strength effective for administration by various means to a patient experiencing an adverse medical condition associated with altered or ineffective lysosomal processing or lysosomal enzyme(s), particularly any of a lysosomal storage disease or associated condition, particularly Gaucher's Disease. A variety of administrative techniques may be utilized, among them parenteral techniques such as subcutaneous, intravenous and intraperitoneal injections, catheterizations and the like. Average quantities of the PGRN fragment and derivative as described herein may vary and in particular should be based upon the recommendations and prescription of a qualified physician or veterinarian.

The peptides and compositions of the invention include those PGRN fragments which are based on the human PGRN sequence, including as set out in FIG. 8C, including SEQ ID NO: 4, as well as variants thereof having one or more or a few or many substitutions, wherein the binding and activity profiles of the variant(s) are retained when compared to PGRN, PGRN peptide or the atsttrin peptide. In as much as PGRN peptides from various animals or mammals, including humans, are known, these sequences provide alternative amino acid sequences and variants of potential use in the compositions and methods of the invention, including by substitution of some of the ND7/Pcgin peptide amino acids. Mouse PGRN sequence is provided herein in FIG. 18B (SEQ ID NO: 3) and corresponding aligned mouse versus human amino acids in amino acids 496-593 are depicted in FIG. 19. Mouse PGRN amino acids corresponding to the amino acid 496-593 region of human PGRN are detailed in FIG. 19 and provided in SEQ ID NO: 6. PGRN sequences for various animals are publicly known and disclosed and would be available for evaluation and assessment in the methods and compositions of the invention, and their corresponding and correlating amino acids suitable for evaluation and use as variants of the PGRN peptides herein. PGRN sequences are available and herein incorporated by reference as follows: rat (Genbank accession AAA16903.1, CAA44198.1), mouse (Genbank accession P28798.2, BAE35389.1, NP_032201.2), Sumatran orangutan (Genbank accession NP_001126689.1), crab-eating macaque (Genbank accession BAE01796.1), horse (Genbank accession XP_001489791.1), cattle (Genbank accession NP_001070482.1), rabbit (Genbank accession XP_002719228.1), pig (Genbank accession NP_001038043.1), chimpanzee (Genbank accession XP_511549.2) and opossum (Genbank accession XP_001374870.1).

Also, antibodies including both polyclonal and monoclonal antibodies, and drugs that modulate the production or activity of PGRN fragment ND7/Pcgin may possess certain diagnostic applications and may for example, be utilized for the purpose of detecting and/or measuring conditions associated with or resulting from altered PGRN, lysosomal storage diseases, Gaucher's disease. For example, the PGRN fragment ND7/Pcgin may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the PGRN of the invention, particularly those which demonstrate binding to lysosomal enzyme, such as binding to GBA, may be discovered or synthesized and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. Panels of monoclonal antibodies produced against PGRN fragment, particularly ND7/Pcgin, can be screened for various properties; i.e., isotype, epitope, affinity, etc. Of particular interest are monoclonal antibodies that neutralize the activity of the PGRN fragment ND7/Pcgin or that bind to GBA. Such monoclonals can be readily identified in binding or activity assays. Preferably, the anti-PGRN fragment ND7/Pcgin antibody used in the diagnostic methods of this invention is an affinity purified polyclonal antibody. More preferably, the antibody is a monoclonal antibody (mAb). In addition, it is preferable for the anti-PGRN antibody molecules used herein be in the form of Fab, Fab', F(ab')$_2$ or F(v) portions of whole antibody molecules.

The invention provides therapeutic methods based upon the activity of PGRN fragment particularly ND7/Pcgin or active variants thereof, in facilitating enzyme delivery to the lysosome, and/or binding or complexing with lysosomal enzymes such as glycocerebrosidase (GBA), or with sortilin and/or HSP70, and/or being capable of reducing lysosomal substrate accumulation, such as β-GlcCer, in the lysosome or macrophage.

Methods are thus provided for facilitating lysosomal delivery of a protein or enzyme in an animal comprising administering to said animal isolated PGRN fragment ND7, or active variants thereof, including variants having at least one, one or more, amino acid substitutions compared to wild type or natural human PGRN sequence of amino acids 496-593. In an aspect thereof said PGRN or active fragment comprises an amino acid sequence as set out in FIG. 8C, including SEQ ID NO: 4. Methods include methods for treating or alleviating a lysosomal storage disease in an animal comprising administering to said animal isolated PGRN fragment ND7/Pcgin, or active variants thereof including substitution of one or more amino acid, including substitution with a corresponding mouse PGRN amino acid sequence, wherein said PGRN or active variant comprises an amino acid sequence as set out in FIG. 8C, or a variant such as having amino acid substitution(s) selected from that depicted in FIG. 19.

In an aspect of these methods, the method comprises additionally administering one or more lysosomal enzyme which is reduced, absent, mutated or altered in the lysosomal storage disease. The lysosomal enzyme may be selected from one or more of a glucocerebrosidase, α-galactosidase, β-galactosidase, β-hexosaminidase and sphingomyelinase. The lysosomal storage disease of the methods of the invention may be selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. In an aspect, the lysosomal storage disease of the methods of the invention may be selected from Gaucher's disease (GD), Tay-sachs disease (TSD), mucolipidosis (ML), mucopolysaccharidosis (MPS), metachromatic leukodystrophy (MLD), Farber disease (FD) and Krabbe disease (KD). In one aspect, the lysosomal storage disease of the methods of the invention may be selected from Gaucher's disease (GD) including GD Type I, II or III, Tay-Sachs disease (TSD), mucolipidosis (ML) including ML III, mucopolysaccharidosis (MPS) including MPS II, III, VI, metachromatic leukodystrophy (MLD), Farber disease (FD) and Krabbe disease (KD). In a particular preferred aspect of the methods of the invention, the lysosomal storage disease (LSD) is Gaucher's Disease (GD). In a particular preferred aspect of the methods of the invention, the lysosomal storage disease (LSD) is Gaucher's Disease (GD). In an aspect of the methods of the invention, the method comprise additionally administering the lysosomal enzyme glycocerebrisidase (GBA) or an active fragment or recombinant form thereof for treating or alleviating Gaucher's Disease. In a particular preferred aspect of the methods of the invention, the lysosomal storage disease (LSD) is Tay-Sachs Disease (TSD).

With regard to the lysosomal storage disease, Gaucher's disease, methods are provided for facilitating delivery of glycocerebrisidase (GBA) in a patient with Gaucher's Disease comprising administering to said patient isolated PGRN fragment or derivative ND7/Pcgin, amino acids 496-593, or active variants thereof. The PGRN or active variant may particularly comprise an amino acid sequence as set out in FIG. 8C, including SEQ ID NO: 4. For Gaucher's Disease in humans, the human PGRN protein or a peptide thereof may particularly be utilized, and may optionally be combined with recombinant human glucocerebrosidase or GBA, such as imiglucerase.

In an aspect of the invention, the PGRN fragment including ND7/Pcgin may be attached to another molecule or may be labeled, including labeled with a detectable label. The label may include or may be selected from radioactive elements, enzymes, chemicals which fluoresce when exposed to ultraviolet light, and others. A number of fluorescent materials are known and can be utilized as labels. These include, for example, fluorescein, rhodamine, lauramine, Texas Red, ACME blue and Lucifer Yellow. The PGRN fragment including ND7/Pcgin can also be labeled with a radioactive element or with an enzyme. The radioactive label can be detected by any of the currently available counting procedures. The isotope may be selected from $^3$H, $^{14}$C, $^{32}$P, $^{36}$Cl, $^{51}$, $^{57}$Co, $^{58}$Co, $^{59}$Fe, $^{90}$, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme may be conjugated to the PGRN fragment by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase.

In an aspect of the invention, the PGRN fragment including ND7/Pcgin may be covalently attached to another molecule or may be a fusion protein. Thus, conjugates or fusion proteins of the present invention, wherein the PGRN fragment including ND7/Pcgin of the present invention are conjugated or attached to other molecules or agents further include, but are not limited to PGRN derivatives or fragments conjugated to a cell targeting agent or sequence, chemical ablation agent, toxin, immunomodulator, cytokine, cytotoxic agent, chemotherapeutic agent or drug.

In an assay, diagnostic method or kit of the invention, a control quantity of the PGRN derivative ND7/Pcgin, GBA/GCase, or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

As suggested earlier, the diagnostic method of the present invention comprises examining a cellular sample or medium by means of an assay including an effective amount of an antagonist to PGRN derivative ND7/Pcgin, such as an anti-PGRN antibody, preferably an affinity-purified polyclonal antibody, and more preferably a mAb. In addition, it is preferable for the antibody molecules used herein be in the form of Fab, Fab', F(ab')$_2$ or F(v) portions or whole antibody molecules. As previously discussed, patients capable of benefiting from this method include those suffering from a lysosomal storage disease or Gaucher's disease. Methods for isolating the antibody and inducing anti-PGRN antibodies and for determining and optimizing the ability of anti-PGRN antibodies to assist in the examination and evaluation of the target cells or of clinical samples are all well-known in the art.

The present invention further contemplates therapeutic compositions useful in practicing the therapeutic methods of this invention. A subject therapeutic composition includes, in admixture, a pharmaceutically acceptable excipient (carrier) and one or more of PGRN fragment ND7 or active variant thereof, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic PGRN fragment-containing compositions are conventionally administered intravenously, as by injection of a unit dose, for example, but may be administered via any suitable means including IM, IP, IV, orally, intranasally, by inhalation, transdermally, etc. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and PGRN activity or PGRN-GBA binding capacity desired. Precise amounts of active ingredient required to be administered depend on the judgment of the practitioner and are peculiar to each individual. However, suitable dosages may range from about 0.001 to 1, 0.01 to 10, 0.1 to 20, 0.5 to 50, preferably about 0.5 to about 10, and more preferably one to several, milligrams of active ingredient per kilogram body weight of individual per day and depend on the route of administration. Suitable regimes for initial administration and subsequent administration are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The present invention naturally contemplates several means for preparation of the PGRN fragment or derivative of the present invention, including as illustrated herein and/or using known recombinant techniques, and the invention is accordingly intended to cover such synthetic preparations within its scope. The determination of the amino acid sequences disclosed herein facilitates the reproduction of the peptides by any of various synthetic methods or any known recombinant techniques, and accordingly, the invention extends to expression vectors comprising nucleic acid encoding the peptides of the present invention for expression in host systems by recombinant DNA techniques, and to the resulting transformed hosts.

The present invention also relates to a recombinant DNA molecule, recombinant nucleic acid, or cloned gene, or a degenerate variant thereof, preferably a nucleic acid molecule, in particular a recombinant DNA molecule or cloned gene, encoding the amino acid of PGRN ND7/Pcgin shown in FIG. 8C or variants thereof. In a particular embodiment, the recombinant DNA molecule, recombinant nucleic acid, or a degenerate variant thereof, preferably a nucleic acid molecule, encodes a PGRN fragment ND7/Pcgin or variant thereof capable of binding GBA, facilitating lysosomal enzyme transport, and/or reducing lysosomal substrate such as β-GlcCer accumulation, which is a fragment of PGRN as depicted in FIG. 8C including comprising a sequence as set out in SEQ ID NO: 4.

As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences— sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

One skilled in the art will be able to select the proper vectors, expression control sequences, and hosts without undue experimentation to accomplish the desired expression without departing from the scope of this invention.

Synthetic DNA sequences allow convenient construction of genes which will express PGRN or atsttrin analogs or "muteins". Alternatively, DNA encoding muteins can be made by site-directed mutagenesis of native PGRN genes or cDNAs, and muteins can be made directly using conventional polypeptide synthesis.

In assays and diagnostic kits of the invention, labels may be used. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The PGRN or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase.

The generation of animal models for lysosomal storage diseases, including Gaucher's Disease, particularly ones that recapitulate the clinical conditions has proven to be a challenge (Farfel-Becker T et al (2011) Dis Model Mech 4(6):746-752). For GD, many GBA knockouts and null mutations in animals have led to lethality or early death (Sun Y et al (2005) J Lipid Res 46:2102-2113). Animal models have been generated based on known GBA mutations, including L449P, N370S, V394L, D409H and D409V point mutations, which are associated with various common forms of GD, as well as chemically induced models, for example involving administration of a GlcCerase inhibitor (Farfel-Becker T et al (2011) Dis Model Mech 4(6):746-752).

Tay-Sachs disease naturally exists in Jacob sheep and the biochemical mechanism for the disease in Jacob Sheep is virtually identical to that in humans (Torres P A, et al (2010) *Molecular Genetics and Metabolism* 101 (4): 357-363). In Jacob sheep, diminished activity of hexosaminidase A resulting in increased concentrations of GM2 ganglioside in the affected animal sheep has been shown (Porter B F, et al (2011) *Veterinary Pathology* 48 (3): 807-813). The sheep HexA gene is identical in number of nucleotides and has 86% nucleotide identity to the human HexA gene. A missense mutation (G444R) was found in the HEXA cDNA of affected sheep, providing a single nucleotide change at the end of exon 11, resulting in that exon's deletion (before translation) via splicing (Kolodny E, Horak F, Horak J (2011) *ALBC Newsletter* (Pittsboro, N.C., USA: American Livestock Breeds Conservancy). Jacob sheep provide an available animal model for Tay-Sachs disease, however, sheep are not as readily manipulated or housed as smaller animals or those with established recombinant methods protocols, such as mice or rats. Therefore, an alternative model for Tay-Sachs in mice, etc would be very beneficial.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Progranulin is Required for the Lysosomal Delivery of β-Glucocerebrosidase and its Deficiency Causes Gaucher Disease In an effort to determine whether PGRN plays a role in chronic lung inflammation, PGRN deficient mice were challenged with ovalbumin (OVA), which led to the discovery of PGRN as an indispensable GBA-associated factor. PGRN was identified as an essential co-chaperone for the lysosomal delivery of GBA through linking GBA/LIMP2 complex to heat shock protein 70 (HSP70), an evolutionarily highly conserved molecular chaperone that mediates the folding and trafficking of numerous proteins. Detailed studies of PGRN full length and atsttrin peptide and Gaucher's disease and other lysosomal storage diseases are provided and described in PCT/US2015/014364 filed Feb. 4, 2015 and U.S. Ser. No. 61/935,541 filed Feb. 4, 2014, which are incorporated herein by reference.

In these prior studies, chronic lung inflammation was induced in 8-week old WT and PGRN knockout (KO) mice by intraperitoneal (IP) injection of OVA at Day 1 and 15, followed by intranasal challenge of 1% OVA beginning at Day 29 three times a week for four weeks. Large numbers of "giant cells" were found in the lungs of PGRN KO mice, particularly after OVA treatment. These cells were engorged with materials with a "wrinkled tissue paper" appearance, the typical morphology of Gaucher cells. A few Gaucher-like cells were identified in unchallenged PGRN KO mice, and the number significantly increased after OVA challenge.

Lipid composition of lung lysates from WT and PGRN KO mice, with or without OVA challenge, was analyzed and β-GlcCer showed increases in all chain-length species in both WT and PGRN KO mice with OVA. Moreover, after OVA challenge all species of β-GlcCer were significantly higher in the PGRN KO vs. WT mice (data not shown). Even untreated PGRN KO mice had a higher level of β-GlcCer than WT mice.

Although GBA is transported to lysosome independently of the mannose-6-phophate receptor (MPR) system, Imiglucerase, a macrophage-targeted, mannose-terminated human GBA for use in enzyme replacement therapy (ERT) for Gaucher's disease, is delivered to lysosome via an MPR-dependent pathway. PGRN KO mice were challenged with OVA, and treated with PBS or imiglucerase injection (60 u/kg/week) at the beginning of the first week of intranasal challenge until the end of the experiment. Following OVA challenge many Gaucher-like cells were present and almost occupied the whole alveolar space, and it was found that Imiglucerase injection significantly decreased the size and accumulation of PAS-positive material as well as β-GlcCer storage in Gaucher-like cells (data not shown). Collectively, these earlier data and the response of the PGRN KO mice to imiglucerase confirmed that OVA-challenged PGRN deficient mice developed the Gaucher's disease phenotype.

Recombinant full length PGRN (rPGRN) rescued the GD-like phenotype seen in PGRN KO animals. An in vitro cell culture model was developed to mimic β-GlcCer accumulation in macrophage in GD. Bone-marrow-derived-macrophage (BMDM) were isolated and differentiated from WT and PGRN KO mice and the cells were treated with 5 and 50 μg/ml brain lysates which contains many types of lipids for 10 days. H&E staining showed that giant macrophages were present in PGRN KO BMDM, but not in WT BMDM and immunofluorescence staining revealed that β-GlcCer was accumulated in PGRN KO BMDM in a dose-dependent manner after lipid mixture treatment.

PGRN full length protein (0.1 and 0.4 μg/ml) protein was added to the culture medium with lipid mixture (50 μg/ml) for 10 days, and the accumulation of β-GlcCer was measured by immunofluorescence staining. Under a light microscope, BMDM after lipid exposure looked enlarged and disorganized with highly retractile cytoplasmic punctate, and this morphological change was corrected by PGRN in a dose-dependent manner. β-GlcCer was accumulated with lipid treatment, and this accumulation was effectively blocked by addition of rPGRN full length and imiglucerase.

The finding that recombinant PGRN prevents GBA aggregation and β-GlcCer accumulation in PGRN KO BMDMs was further confirmed with fibroblasts from GD patients. Fibroblasts from type II GD patients were treated with 50 μg/ml lipid mixture with or without 0.4 μg/ml rPGRN full length. GBA became aggregated around nucleus accompanied with β-GlcCer accumulation following lipid treatment, and all these phenotypes were markedly inhibited by addition of rPGRN (data not shown).

Studies to assess whether rPGRN full length could also rescue the GD phenotype in vivo were conducted. PGRN KO mice challenged with OVA were I.P. injected with either PBS or rPGRN (4 mg/kg per week) from the first week of starting the intranasal challenge until to the end of the experiment. Histology of lung tissues showed infiltration with Gaucher-like cells induced by OVA challenge in PGRN KO mice, and rPGRN dramatically reversed the phenotype. Unlike Imiglucerase treatment which reduced size without a significant effect on the number of Gaucher-like cells, rPGRN significantly decreased both number and size of Gaucher-like cells, indicating that PGRN inhibited both Gaucher-like cells formation and β-GlcCer accumulation.

Accumulation of β-GlcCer in GD is caused by reduced GBA enzymatic activity or decreased GBA protein expression. Although the protein level and activity of GBA were not decreased in PGRN KO, immunohistochemistry staining of GBA revealed that GBA cellular distribution was dramatically altered. Immunogold labeling TEM demonstrated that GBA was aggregated in the cytoplasm in Gaucher-like cells, and GBA was absent in the tubular-like lysosomes in PGRN null macrophages, while GBA was detectable in lysosomes in WT macrophages. In addition, recombinant PGRN rescued the lysosomal appearance of GBA in PGRN-deficient macrophages. Taken together, these earlier results demonstrate that the delivery of GBA to the lysosome depends on the presence of PGRN.

Lysosomal integral membrane protein 2 (LIMP2), a lysosomal marker, was reported to function as a GBA-binding receptor that mediated the delivery of GBA to lysosomes[31,32]. Interestingly, it was found that lysosomal delivery of LIMP2 was also defective in PGRN-deficient macrophages.

In vivo interaction between PGRN and GBA was demonstrated by co-immunoprecipitation by using GBA antibody to immunoprecipitate the protein complex and probing with PGRN antibody. PGRN demonstrated dose-dependent binding and saturation to liquid-phase GBA, whereas no direct interaction between PGRN and LIMP2 was detected (data not shown). The binding affinity between PGRN and GBA was then measured using surface plasmon resonance (SPR) with SensiQ Pioneer as described[13,14]. The results demonstrated that PGRN binds to GBA with a very high affinity ($K_D$=0.71 nM) (FIG. 14C), higher than PGRN's affinity to Sortilin ($K_D$=3.67 nM) (not shown), a known PGRN-binding lysosomal receptor[26].

These data were followed up with studies in HEK293EBAN cells stably transfected with an expression plasmid encoding His-tagged PGRN[13]. Two proteins were co-purified with His-tagged PGRN, and MS analysis revealed that these were HSP70 and TCP1 (not shown). Previous reports that LIMP2 was the major GBA transport receptor[31,34,35], together with the finding that both GBA and LIMP2 were aggregated in PGRN deficient macrophages, led to determination whether HSP70 also interacted with LIMP2. Similar to GBA, LIMP2 also associated with HSP70 in WT but not in PGRN KO tissues. Sortilin was reported to be a receptor of PGRN and to mediate the delivery of PGRN to the endosome/lysosomal pathway in neurons[26]. It was thus determined whether Sortilin forms a ternary complex with LIMP2/GBA/PGRN/HSP70 through PGRN as a linker protein and facilitates the delivery of LIMP2/GBA/PGRN/HSP70 along the endosome/lysosomal pathway and it was found that this was the case. Collectively, Sortilin associates with LIMP2/GBA/PGRN/HSP70 complex through PGRN as an indispensable adaptor.

It was examined whether PGRN would have therapeutic effects in GDs and other LSDs. Using the similar lysotracker approach[37], the effects of rPGRN full length was assessed on fibroblasts from normal and 11 different patient fibroblasts of LSDs, including GDs. As expected, PGRN effectively reverted the altered lysosomes in fibroblasts from both Type I and II GD with or without lipid stimulation, and PGRN also remarkably normalized the altered lysosomes in fibroblasts of Tay-Sachs disease, Farber disease, and Mucolipidosis III. The accumulation of GAG and M2 ganglioside was also observed in the tissues from aged PGRN deficient mice (data not shown). In the case of type III GD, Mucopolysacharidosis III and VI, PGRN demonstrated beneficial effects in the presence of lipid stimulation Taken together, these earlier results implicate full length PGRN, as a co-chaperone of HSP70 trafficking pathway, as involved in the lysosomal delivery of other lysosome enzymes in addition to GBA.

Materials and Methods

Materials: Fibroblasts from type I, II and III GD, Tay-Sachs disease, Farber disease, type IV and IV mucolipidosis (ML), type III and VI mucopolysaccharidosis (MPS), Niemann-Pick disease type B, and Fabry disease were purchased from Coriell Cell Repositories (Camden, N.J.), and normal fibroblasts were purchased from Gibico. All fibroblasts were cultured in DMEM medium containing 10% FBS. Antibodies against GBA (sc-100544, sc-30844, and sc-32883), PGRN (SC-28928), Sortilin (sc-376576), α-GLA (sc-25823), HSP70 (sc-373867), Calregulin (sc-373863), TGN38 (sc-271624), EEA1 (sc-365652) LIMP2 (sc-55571), and LAMP2 (sc-18822), were purchased from Santa Cruz Biotechnology (Dallas, Tex.). β-GlcCer antibody (Cat. No. RAS_0010) was purchased from Glycobiotech GmbH (Germany). Donkey anti-Mouse IgG labeled with Alexa Fluor® 488, Alexa Fluor 647, or Cyanine cy3, and donkey anti-Rabbit labeled with Alexa Fluor® 488, or Cyanine cy3, and Donkey anti-sheep IgG labeled with Alexa Fluor 488, or Cyanine cy3 were purchased from Jackson ImmunoResearch Laboratories, Inc. (West Grove, Pa.). Recombinant His-tag PGRN protein was purified from 293T stable cell lines as described previously[13,14]. Recombinant GBA (Cat. No. 7410-GH-010), sortilin (Cat. No. 3154-ST-050), and LIMP2 (Cat. No. 1966-LM-050) proteins and sheep anti-mouse PGRN antibody (AF2557) were purchased from R&D Systems (Minneapolis, Minn.). Human PGRN ELISA kit was purchased from AdipoGen (San Diego, Calif.). ERK inhibitor PD98059, PI3K inhibitor Wortmannin and mTOR inhibitor rapamycin were purchased from Life Technologies. Imiglucerase was provided by Dr. Pastores.

Chronic lung inflammation model: C57B/L6 WT and PGRN KO mice were hosted in the animal facility of New York University as previously described_ENREF_1[13,55]. 8 weeks-old mice were induced chronic lung inflammation by I.P. injection of OVA-Alum challenged at Day 1 and Day 15, followed by followed by intranasal challenge of 1% OVA beginning at Day 29 three times a week for four weeks_ENREF_3[51]_ENREF_3. In PGRN rescue experiments frequency of intranasal challenge of OVA was increased to three times a week. The mice were sacrificed, and spleen, liver, leg, lung and bronchoalveolar lavage (BAL) were collected. In the PGRN rescue experiments, 4 mg/kg of recombinant PGRN or 60 u/kg imiglucerase were I.P injected every week when intranasal challenge started.

In another experiment, WT and PGRN KO mice were hosted in animal facility of New York University until 1 year-old. Aged mice were sacrificed directly, and lung, spleen, liver, femur, and spine were collected for histology and micro-CT analysis.

Transmission electron microscope (TEM): WT and PGRN KO mice after OVA treatment, as well as aged PGRN KO mouse, were anesthetized and the lung was perfuse fixed with fixative containing 2.5% Glutaraldehyde and 2% paraformaldehyde in 0.1M sodium cacodylate buffer (pH 7.2) for 2 hours. After washing, the samples were fixed in 1% OsO4 for 1 hour, block staining with 1% uranyl acetate for 1 hour, dehydration and embedded in Embed 812 (Electron Microscopy Sciences, Hatfield, Pa.). 60 nm sections were cut, and stained with uranyl acetate and lead citrate by standard methods. Stained grids were examined under Philips CM-12 electron microscope (FEI; Eindhoven, The Netherlands) and photographed with a Gatan (4k×2.7k) digital camera (Gatan, Inc., Pleasanton, Calif.).

For immunoelectron microscopy, mice were perfused and fixed with 4% PFA in 0.1M phosphate buffer (pH7.4), and the lung was dissected and continuously fixed in the freshly made 3% PFA in 0.1M phosphate buffer containing 0.1% glutaraldehyde and 4% sucrose (pH 7.4). After washing and dehydration, the tissue were embedded in Lowicryl K4M (Polysciences, Inc., Warrington, Pa.) and LR White (Electron Microscopy Sciences, Hatfield, Pa.). Polymerized will be under UV light (360 nm) at −35° C. for LK4M and −10° C. for LR White. Ultrathin sections were cut, mounted on Formvar-Carbon coated nickel grids. After incubation with primary antibodies at 4° C. overnight, gold conjugated secondary antibodies (15 nm Protein A Gold, Cell Microscopy Center, University Medical Center Utrecht, 35584 CX Utrecht, The Netherlands; 18 nm Colloidal Gold-AffiniPure Goat Anti-Rabbit IgG (H+L), Jackson ImmunoReasearch Laboratories, Inc., West Grove, Pa.) were applied. The grids were stained with uranyl acetate and lead citrate by standard methods, and examined under Philips CM-12 electron microscope (FEI; Eindhoven, The Netherlands) and photographed with a Gatan (4k×2.7k) digital camera (Gatan, Inc., Pleasanton, Calif.).

Immunofluorescence staining and Confocal Microscope: Frozen lung sections, or cover-slip cultured BMDM, were fixed with 4% formaldehydrate for 5 min and washed twice with PBS. The cells were permeabilized by 0.1% Triton-100 PBS for 5 min and then wash with PBS. The tissues were blocked with 1:50 dilution of normal donkey serum for 30 min. Primary antibodies were probed on the slides at 4° C. degree overnight. The next day slides were washed with PBS, fluorescence-labeled secondary antibodies (Alexa Fluor® 488-labeled donkey anti-mouse combined with Cyanine cy3-labeled donkey anti-rabbit antibody, or in some experiments different fluorescence were used) were added for 1 hour and wash with PBS. The tissues or BMDM cells were mounted on anti-fade medium containing DAPI. The images were taken by Leica TCS SP5 con-focal system.

Flow cytometry: BAL was collected when mice were sacrificed, and centrifuged at 1200 rpm for 5 min to collect cells. The cells were suspended and washed in ice-cold PBS containing 0.1% FBS for two times. The cells were stained with FITC-labeled CD11b antibody (eBioscience San Diego, Calif.) for 1 hour and analyzed by BD FACScan, and data were analyzed by FlowJo software.

Micro-CT: The trabecular volume in the distal femoral metaphysis was measured using a Scanco µCT40 scanner (Scanco Medical AG, Basserdorf, Switzerland). A threshold of 300 was used for evaluation of all scans. 30 slices were analyzed, starting with the first slice in which condyles and primary spongiosa were no longer visible.

Immunoprecipitation: Lung tissue from OVA-challenged or -unchallenged WT and PGRN KO mice with or without with or without rPGRN treatment were lysed by RIPA lysis buffer containing protease inhibitors. 12000 rpm centrifuge 10 min to pellet the debris. The supernatant were transferred to a new tube and 10 seconds supersonic pulse were used to further release membrane proteins. Same amount of proteins from each group of mouse were mixed together to represent the protein profile of each group. 400 µg protein from mixed samples were used for immunoprecipitation. 2 µg/ml normal mouse and rabbit antibodies and 20 µl protein A/G agarose-beads were added, and incubated 1 hour at 4° C. Centrifuge at 3000 rpm for 5 min to pellet the beads. The supernatant were transferred to a new tube and 2 µg/ml primary antibodies were added and incubated 1 hour at 4° C., then 20 µl protein A/G agarose-beads were added and incubated overnight. The beads were washed with RIPA lysis buffer 6-8 times, the samples were run on SDS-PAGE, and targeted proteins were probed with antibody and visualized by western-blot. In some experiments, the samples after immunoprecipitation were sent to NYU core facility to do Mass Spectrometry.

Immunohistochemistry: Paraffin-embedded lung slides from WT and PGRN KO mice de-paraffined by xylene and gradient ethanol. Antigen was retrieved by using 0.1% trypsin (diluted from 0.5% trypsin by 0.1% $CaCl_2$) at 37° C. for 30 min. Endogenous hydrogen peroxidase was inactivated by 3% $H_2O_2$ in PBS for 10 minutes. The slides were blocked with 3% BSA and 20% goat serum for 30 minutes. Primary antibodies were diluted at 1:20-50 with 2% goat serum, primed on the slides at 4° C. overnight. The next day slides were washed with PBS and secondary antibody were added (1:200 biotin-labeled goat-anti rabbit antibody or goat-anti mouse antibody) for 1 hour. The staining was visualized by Vector ABC peroxidase kit, followed by DAB substrates.

Mass spectrum: 1) Gel Separation and Digestion. Samples were reduced with DTT at 57° C. for 1 hour and were alkylated with Iodoacetamide at RT in the dark for 45 minutes. Each sample was loaded onto a NuPAGE® 4-12% Bis-Tris Gel 1.0 mm The gel was stained using GelCode Blue Stain Reagent (Thermo Scientific) and Coomassie stained gel bands were excised as indicated on the gel image. Excised gel pieces were destained with a 50:50 v/v solution of methanol and 100 mM ammonium bicarbonate. The gel pieces were partially dehydrated with an acetonitrile rinse and further dried in a SpeedVac concentrator for 20 minutes. 300 ng of sequencing grade modified trypsin (Promega) were added to each gel sample. After the trypsin was absorbed 100 μl of 100 mM ammonium bicarbonate was added to cover the gel pieces. Digestion proceeded overnight on a shaker at RT.

(2) Protein Extraction. A slurry of R2 20 μm Poros beads (Life Technologies Corporation) in 5% formic acid and 0.2% trifluoroacetic acid (TFA) was added to each sample at an volume equal to that of the ammonium bicarbonate added for digestion. The samples shook at 4° C. for 2 hours. The beads were loaded onto equilibrated C18 ziptips (Millipore) using a microcentrifuge for 30 seconds at 6000 rpm. Gel pieces were rinsed three times with 0.1% TFA and each rinse was added to its corresponding ziptip followed by microcentrifugation. The extracted porors beads were further washed with 0.5% acetic acid Peptides were eluted by the addition of 40% acetonitrile in 0.5% acetic acid followed by the addition of 80% acetonitrile in 0.5% acetic acid. The organic solvent was removed using a SpeedVac concentrator and the sample reconstituted in 0.5% acetic acid.

MS Analysis. ⅕th of each sample was analyzed individually with the mIgG analyzed first, then the KO GBA, and finally the WT GBA. Samples were injected for on-line LC-MS using the autosampler of a EASY-nLC 1000 (Thermo Scientific). Peptides were gradient eluted from the column directly to Q Exactive mass spectrometer (Thermo Scientific) using a 1 hour gradient Solvent A: 5% acetonitrile, 0.5% acetic acid Solvent B: 95% acetonitrile, 0.5% acetic acid.

MS Method. High resolution full MS spectra were acquired with a resolution of 70,000, an AGC target of 1e6, with a maximum ion time of 120 ms, and scan range of 300 to 1500 m/z. Following each full MS twenty data-dependent high resolution HCD MS/MS spectra were acquired. All MS/MS spectra were collected using the following instrument parameters: resolution of 17,000, AGC target of 2e5, maximum ion time of 250 ms, one microscan, 2 m/z isolation window, fixed first mass of 150 m/z, and NCE of 27. MS/MS spectra were searched against a uniprot mouse database using Sequest within Proteome Discoverer.

Surface Plasmon Resonance (SPR): All SPR experiments were done by SensiQ Technologies Inc. (Oklahoma City, Okla.) by using SensiQ Pioneer at a controlled analysis temperature of 25° C., and samples in the instrument sample racks were maintained at 18° C. The running buffer throughout the immobilization and the assay consisted of 10 mM HEPES, 150 mM NaCl, 0.005% Tween 20. Buffer pH was adjusted to pH 7.4, 6.5, 6.0 or 5.5 for individual runs, and for each pH the running buffer was used to prepare PGRN samples and sucrose diffusion standards.

A COOH1 chip was installed and conditioned via 10 second injections (2× each) of 10 mM HCl, 50 mM NaOH, and 0.1% SDS. Channel 3 was activated via a five minute injection of 4 mM EDC and 1 mM NHS in water at a 20 uL/min flow rate. GBA (25 ug/mL in 10 mM sodium acetate pH 5.5) was then injected for ~two minutes at a 10 uL/min flow rate. Channels 1 and 2 were then activated with 4 mM EDC and 1 mM NHS in water for five minutes. Sortilin (10 ug/mL in sodium acetate pH 4.0) was immobilized on channel 1 via a five minute injection at a 10 uL/min flow rate. BSA (10 ug/mL in sodium acetate pH 4.3) was immobilized on the reference channel to reduce non-specific binding. All channels were capped with a four minute injection of 1M Ethanolamine pH8.0.

The assay of PGRN was performed with a total of five buffer blank injections and two replicates of 200 nM PGRN, all of which were given a 1 hour dissociation time. The OneStep™ injection was used for this assay to determine kinetic rate constants and the equilibrium dissociation constant from a single gradient inject. Two injections of 3% sucrose in running buffer were performed to serve as a diffusion standard.

Data was analyzed using the QDat Analysis Software (SensiQ Technologies and BioLogic Software). All data were double referenced to a reference channel (channel 2) and buffer blanks. The average signal of the buffer blanks was used to subtract injection artifacts. Referenced SPR data from the analysis channels were model fit to ascertain ka, kd, and $K_D$ for the interactions.

Solid phase binding: 0.1, 1, 2, and 5 μg/ml PGRN proteins were coated in 96-wells with triplicate wells in PBS for overnight. The plate was washed with 0.1% tween/PBS five times and then blocked with 2% BSA/PBS solution. Two μg BSA, LIMP2 and GBA protein were labeled with biotin followed the protocol of EZ-Link Sulfo-NHS-LC-Biotin and Biotinylation Kits (Thermo Scientific). Biotin-labeled LIMP2, GBA or BSA were added in the plate and incubate for 2 hours. Wash with 0.1% tween/PBS, and coated with streptavidin-HRP (1:2000 dilution) solution for 1 hour. After washing add t h e substrate and stop the reaction with 100 μM $H_2SO_4$. Read result at UV 450 nm in plate reader.

BMDM differentiation and in vitro GD model: Differentiation of BMDMs was performed by following protocol reported previously[25,53]. Briefly monocytes were isolated from WT and KO bone marrow and cultured in RPMI1640, supplemented with L929 condition medium for 5 days to differentiation into macrophages. To mimic development of Gaucher cells in vitro, 50 μg/ml brain lysates (1 g of mouse brain tissues were homogenized in 10 ml of DMEM medium by Bio-Gen PRO200 Homogenizer from 1 min at highest speed) containing various kinds of lipids, including sphingolipid, were added in the cell culture supernatant for 10 days. In the case of the in vitro rescue experiments, 0.1 and 0.4 μg/ml PGRN were added at the same time with lipid.

Cell culture mediums were replenished every three days. The levels of β-GlcCer were stained by immunofluorescence staining.

Fluorescence labeling of active form of lysosomal GBA: MDW933, a specific sensitive fluorescence dye for labeling active lysosomal GBA[28,30], was generously provided by Dr. Hermen E. Overkleeft at University of Leiden. BMDMs were cultured on cover glass, and MDW933 (50 nM) were added in culture medium for 2 hours to label lysosomal GBA. Cells were then fixed with 3% (v/v) paraformaldehyde in PBS for 15 min, and permeabilized by 0.1 mM $NH_4Cl$ in PBS for 10 min. BMDMs were mounted with DAPI-medium, and fluorescence were visualized under confocal microscope.

Lysosome staining in LSD fibroblasts: Fibroblasts from different LSDs and healthy control were cultured on coverslip in 24-well plates in the absence or presence of recombinant PGRN protein (0.4 μg/ml), lipid lysis (50 μg/ml), and PGRN plus lipid lysis for 24 hours. The next day fresh medium containing 100 nM LysoTracker® Red was added for 1 hour. The cells were washed with PBS and fixed in 2% PFA. The coverslips were mounted on slides and the staining of lysosomes was imaged by confocal microscopy. Ten images were randomly taken from each sample, and fluorescence intensities were measured by Image J software.

REFERENCES

1 Brady, R. O., Kanfer, J. N. & Shapiro, D. Metabolism of Glucocerebrosides. Ii. Evidence of an Enzymatic Deficiency in Gaucher's Disease. *Biochemical and biophysical research communications* 18, 221-225 (1965).

2 Platt, F. M. Sphingolipid lysosomal storage disorders. *Nature* 510, 68-75, doi:10.1038/nature13476 (2014).

3 Beutler, E. Gaucher's disease. *The New England journal of medicine* 325, 1354-1360, doi:10.1056/NEJM199111073251906 (1991).

4 Hrabal, R., Chen, Z., James, S., Bennett, H. P. & Ni, F. The hairpin stack fold, a novel protein architecture for a new family of protein growth factors. *Nat Struct Biol* 3, 747-752 (1996).

5 Bateman, A. & Bennett, H. P. The granulin gene family: from cancer to dementia. *BioEssays: news and reviews in molecular, cellular and developmental biology* 31, 1245-1254, doi:10.1002/bies.200900086 (2009).

6 He, Z., Ong, C. H., Halper, J. & Bateman, A. Progranulin is a mediator of the wound response. *Nat Med* 9, 225-229, doi:10.1038/nm816 (2003).

7 Zhu, J. et al. Conversion of proepithelin to epithelins: roles of SLPI and elastase in host defense and wound repair. *Cell* 111, 867-878 (2002).

8 Jian, J., Konopka, J. & Liu, C. Insights into the role of progranulin in immunity, infection, and inflammation. *Journal of leukocyte biology* 93, 199-208, doi:10.1189/jlb.0812429 (2013).

9 Baker, M. et al. Mutations in progranulin cause tau-negative frontotemporal dementia linked to chromosome 17. *Nature* 442, 916-919, doi:10.1038/nature05016 (2006).

10 Cruts, M. et al. Null mutations in progranulin cause ubiquitin-positive frontotemporal dementia linked to chromosome 17q21. *Nature* 442, 920-924, doi:10.1038/nature05017 (2006).

11 Ahmed, Z. et al. Accelerated lipofuscinosis and ubiquitination in granulin knockout mice suggest a role for progranulin in successful aging. *The American journal of pathology* 177, 311-324, doi:10.2353/ajpath.2010.090915 (2010).

12 Gotzl, J. K. et al. Common pathobiochemical hallmarks of progranulin-associated frontotemporal lobar degeneration and neuronal ceroid lipofuscinosis. *Acta Neuropathol,* doi:10.1007/s00401-014-1262-6 (2014).

13 Tang, W. et al. The growth factor progranulin binds to TNF receptors and is therapeutic against inflammatory arthritis in mice. *Science* 332, 478-484, doi:10.1126/science.1199214 (2011).

14 Jian, J. et al. Progranulin directly binds to the CRD2 and CRD3 of TNFR extracellular domains. *FEBS letters,* doi:10.1016/j.febslet.2013.09.024 (2013).

15 Liu, C., Li, X. X., Gao, W., Liu, W. & Liu, D. S. Progranulin-Derived Atsttrin Directly Binds to TNFRSF25 (DR3) and Inhibits TNF-Like Ligand 1A (TL1A) Activity. *PloS one* 9, e92743, doi:10.1371/journal.pone.0092743 (2014).

16 Li, M. et al. Progranulin is required for proper ER stress response and inhibits ER stress-mediated apoptosis through TNFR2. *Cell Signal* 26, 1539-1548, doi:10.1016/j.cellsig.2014.03.026 (2014).

17 Thurner, L. et al. Progranulin antibodies entertain a proinflammatory environment in a subgroup of patients with psoriatic arthritis. *Arthritis research & therapy* 15, R211, doi:10.1186/ar4406 (2013).

18 Thurner, L. et al. Proinflammatory Progranulin Antibodies in Inflammatory Bowel Diseases. *Digestive diseases and sciences,* doi:10.1007/s10620-014-3089-3 (2014).

19 Rothman, J. E. & Schekman, R. Molecular mechanism of protein folding in the cell. *Cell* 146, 851-854, doi:10.1016/j.cell.2011.08.041 (2011).

20 Grabowski, G. A. Gaucher disease and other storage disorders. Hematology/the *Education Program of the American Society of Hematology. American Society of Hematology. Education Program* 2012, 13-18, doi:10.1182/asheducation-2012.1.13 (2012).

21 Mazzulli, J. R. et al. Gaucher disease glucocerebrosidase and alpha-synuclein form a bidirectional pathogenic loop in synucleinopathies. *Cell* 146, 37-52, doi:10.1016/j.cell.2011.06.001 (2011).

22 Aerts, J. M. et al. Glucocerebrosidase, a lysosomal enzyme that does not undergo oligosaccharide phosphorylation. *Biochimica et biophysica acta* 964, 303-308 (1988).

23 Van Weely, S. et al. Function of oligosaccharide modification in glucocerebrosidase, a membrane-associated lysosomal hydrolase. *European journal of biochemistry/FEBS* 191, 669-677 (1990).

24 Xu, Y. H., Sun, Y., Barnes, S. & Grabowski, G. A. Comparative therapeutic effects of velaglucerase alfa and imiglucerase in a Gaucher disease mouse model. *PloS one* 5, e10750, doi:10.1371/journal.pone.0010750 (2010).

25 Hu, X. et al. IFN-gamma suppresses IL-10 production and synergizes with TLR2 by regulating GSK3 and CREB/AP-1 proteins. *Immunity* 24, 563-574, doi:10.1016/j.immuni.2006.02.014 (2006).

26 Hu, F. et al. Sortilin-mediated endocytosis determines levels of the frontotemporal dementia protein, progranulin. *Neuron* 68, 654-667, doi:10.1016/j.neuron.2010.09.034 (2010).

27 Prabakaran, T. et al. Mannose 6-phosphate receptor and sortilin mediated endocytosis of alpha-galactosidase A in kidney endothelial cells. *PloS one* 7, e39975, doi:10.1371/journal.pone.0039975 (2012).

28 Witte, M. D. et al. Ultrasensitive in situ visualization of active glucocerebrosidase molecules. *Nature chemical biology* 6, 907-913, doi:10.1038/nchembio.466 (2010).

29 Aerts, J. M. et al. Biomarkers in the diagnosis of lysosomal storage disorders: proteins, lipids, and inhibodies. *Journal of inherited metabolic disease* 34, 605-619, doi:10.1007/s10545-011-9308-6 (2011).

30 Gaspar, P. et al. Action myoclonus-renal failure syndrome: diagnostic applications of activity-based probes and lipid analysis. *Journal of lipid research* 55, 138-145, doi:10.1194/jlr.M043802 (2014).

31 Reczek, D. et al. LIMP-2 is a receptor for lysosomal mannose-6-phosphate-independent targeting of beta-glucocerebrosidase. *Cell* 131, 770-783, doi:10.1016/j.cell.2007.10.018 (2007).

32 Neculai, D. et al. Structure of LIMP-2 provides functional insights with implications for SR-BI and CD36. *Nature* 504, 172-176, doi:10.1038/nature12684 (2013).

33 Gonzalez, E. M., Mongiat, M., Slater, S. J., Baffa, R. & Iozzo, R. V. A novel interaction between perlecan protein core and progranulin: potential effects on tumor growth. *J Biol Chem* 278, 38113-38116 (2003).

34 Saftig, P. & Klumperman, J. Lysosome biogenesis and lysosomal membrane proteins: trafficking meets function. *Nature reviews. Molecular cell biology* 10, 623-635, doi:10.1038/nrm2745 (2009).

35 Blanz, J. et al. Disease-causing mutations within the lysosomal integral membrane protein type 2 (LIMP-2) reveal the nature of binding to its ligand beta-glucocerebrosidase. *Human molecular genetics* 19, 563-572, doi:10.1093/hmg/ddp523 (2010).

36 Yang, C. et al. Celastrol increases glucocerebrosidase activity in Gaucher disease by modulating molecular chaperones. *Proceedings of the National Academy of Sciences of the United States of America* 111, 249-254, doi:10.1073/pnas.1321341111 (2014).

37 Kirkegaard, T. et al. Hsp70 stabilizes lysosomes and reverts Niemann-Pick disease-associated lysosomal pathology. *Nature* 463, 549-553, doi:10.1038/nature08710 (2010).

38 Tanaka, Y., Matsuwaki, T., Yamanouchi, K. & Nishihara, M. Increased lysosomal biogenesis in activated microglia and exacerbated neuronal damage after traumatic brain injury in progranulin-deficient mice. *Neuroscience* 250, 8-19, doi:10.1016/j.neuroscience.2013.06.049 (2013).

39 Farfel-Becker, T., Vitner, E. B. & Futerman, A. H. Animal models for Gaucher disease research. *Disease models & mechanisms* 4, 746-752, doi:10.1242/dmm.008185 (2011).

40 Lu, J. et al. Histone deacetylase inhibitors prevent the degradation and restore the activity of glucocerebrosidase in Gaucher disease. *Proceedings of the National Academy of Sciences of the United States of America* 108, 21200-21205, doi:10.1073/pnas.1119181109 (2011).

41 Ingemann, L. & Kirkegaard, T. Lysosomal Storage Diseases and the Heat Shock Response: Convergences and Therapeutic Opportunities. *Journal of lipid research, doi:* 10.1194/jlr.R048090 (2014).

42 Almeida, S., Zhou, L. & Gao, F. B. Progranulin, a glycoprotein deficient in frontotemporal dementia, is a novel substrate of several protein disulfide isomerase family proteins. *PloS one* 6, e26454, doi:10.1371/journal.pone.0026454 (2011).

43 Mu, T. W. et al. Chemical and biological approaches synergize to ameliorate protein-folding diseases. *Cell* 134, 769-781, doi:10.1016/j.cell.2008.06.037 (2008).

44 Wei, H. et al. E R and oxidative stresses are common mediators of apoptosis in both neurodegenerative and non-neurodegenerative lysosomal storage disorders and are alleviated by chemical chaperones. *Human molecular genetics* 17, 469-477, doi:10.1093/hmg/ddm324 (2008).

45 Tanaka, Y., Chambers, J. K., Matsuwaki, T., Yamanouchi, K. & Nishihara, M. Possible involvement of lysosomal dysfunction in pathological changes of the brain in aged progranulin-deficient mice. *Acta neuropathologica communications* 2, 78, doi:10.1186/PREACCEPT-4589926441299369 (2014).

46 Vitner, E. B. et al. RIPK3 as a potential therapeutic target for Gaucher's disease. *Nat Med* 20, 204-208, doi:10.1038/nm.3449 (2014).

47 Petkau, T. L. & Leavitt, B. R. Progranulin in neurodegenerative disease. *Trends in neurosciences, doi:*10.1016/j.tins.2014.04.003 (2014).

48 Leverenz, J. B. et al. A novel progranulin mutation associated with variable clinical presentation and tau, TDP43 and alpha-synuclein pathology. *Brain: a journal of neurology* 130, 1360-1374, doi:10.1093/brain/awm069 (2007).

49 Platt, F. M., Boland, B. & van der Spoel, A. C. The cell biology of disease: lysosomal storage disorders: the cellular impact of lysosomal dysfunction. *The Journal of cell biology* 199, 723-734, doi:10.1083/jcb.201208152 (2012).

50 Eblan, M. J., Walker, J. M. & Sidransky, E. The glucocerebrosidase gene and Parkinson's disease in Ashkenazi Jews. *The New England journal of medicine* 352, 728-731; author reply 728-731, doi:10.1056/NEJM200502173520719 (2005).

51 Daley, E. et al. Pulmonary arterial remodeling induced by a Th2 immune response. *J Exp Med* 205, 361-372, doi: 10.1084/jem.20071008 (2008).

52 Fabrega, S. et al. Human glucocerebrosidase: heterologous expression of active site mutants in murine null cells. *Glycobiology* 10, 1217-1224 (2000).

53 Weischenfeldt, J. & Porse, B. Bone Marrow-Derived Macrophages (BMM): Isolation and Applications. *CSH protocols* 2008, pdb prot5080, doi:10.1101/pdb.prot5080 (2008).

54 Eid, J. et al. Real-time DNA sequencing from single polymerase molecules. *Science* 323, 133-138, doi: 10.1126/science.1162986 (2009).

55 Yin, F. et al. Exaggerated inflammation, impaired host defense, and neuropathology in progranulin-deficient mice. *J Exp Med* 207(1):117-128 (2010).

Example 2

Evaluation of PGRN Serial Deletions

Although PGRN is therapeutic against GD in multiple models described above, there is concern for the long-term usage of PGRN as a drug because PGRN growth factor has oncogenic activity and its levels are higher in various kinds of cancer tissues than their healthy counterparts (Bateman and Bennett, 2009; He and Bateman, 1999; He et al., 2002). To address this issue, we devoted considerable effort toward developing a PGRN-derived molecule that retains the GCase (GBA)-binding and therapeutic activity of PGRN but lacks its oncogenic action. For this purpose, numerous PGRN mutants (i.e., C-terminal deletions, N-terminal deletions, internal deletions, and various combinations) were generated, and their interactions with GCase were tested. In order to assess the PGRN peptide region or regions involved in GBA binding and lysosomal protein traffic and to evaluate derivative molecules for alleviation and treatment of lysosomal storage disease(s), serial deletions from the N-terminal and from the C-terminal of PGRN were initially constructed and evaluated.

A series of N-terminal deletion mutants were first constructed. The scheme of constructs encoding serial GFP-tagged N-terminal deletion mutants is shown in FIG. 2A. The PGRN amino acids remaining in each deletion mutant are as follows: ND1 (aa 45-593), ND2 (aa 113-593), ND3 (aa 179-593), ND4 (aa 261-593), ND5 (aa 336-593), ND6 (aa 416-593), and ND7 (aa 496-593). Expression of each of the GFP-tagged N-terminal deletion PGRN fragments was confirmed by immunoblotting with anti-GFP antibody. All deletion mutants were expressed as shown in FIG. 2B.

Figure 3:
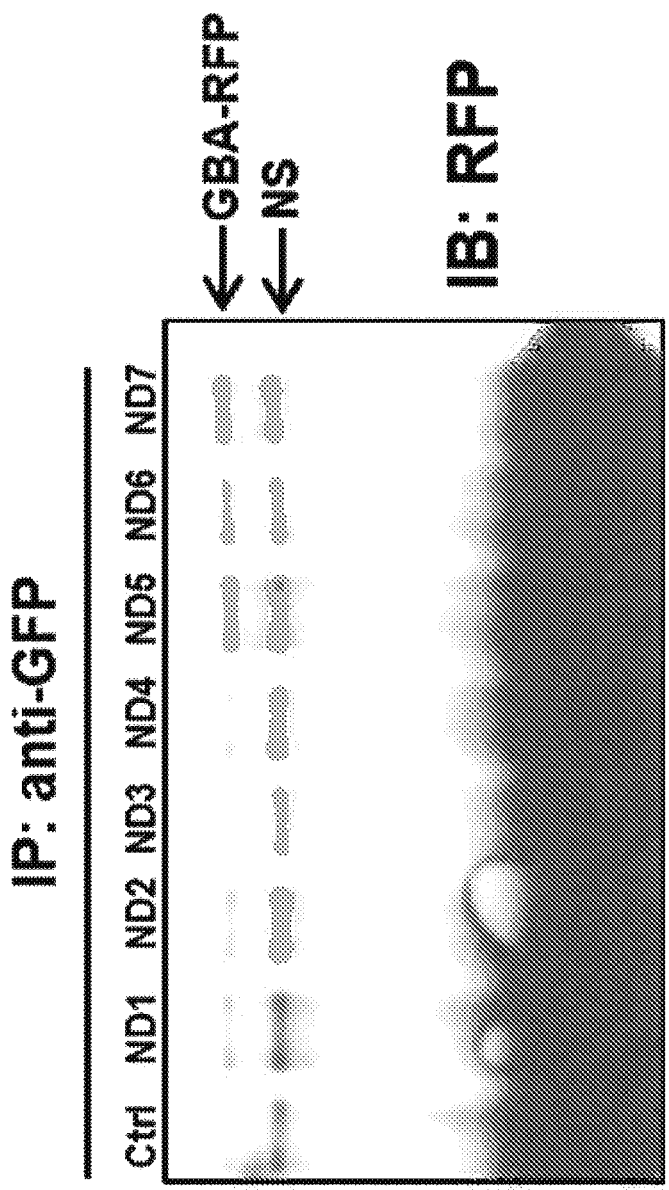
FIG. 3 shows binding of GBA to PGRN N-terminal serial deletions fragments by co-IP assay. 293 EBNA cells were transfected with pDsRed-GBA encoding RFP-fused GBA and corresponding plasmids encoding various GFP-fused N-terminal deletions of PGRN, as indicated, and the cell lysates were immunoprecipitated with GFP antibody. The complexes were probed with anti-RFP antibody. Control IgG (Ctrl) used as a negative control. NS indicates non-specific binding.

Next, binding of glucocerebrosidase (GBA) to PGRN N-terminal serial deletions fragments was assessed using a co-IP assay (FIG. 3). 293 EBNA cells were co-transfected with pDsRed-GBA, which encodes RFP-fused GBA, and also corresponding plasmids encoding the various GFP-fused N-terminal deletions of PGRN. Cell lysates from each combination were immunoprecipitated with GFP antibody and the complexes were probed with anti-RFP antibody. Control IgG (Ctrl) was used as a negative control. As shown in FIG. 3, the N-terminal serial deletions bound GBA, although ND3 binding was less compared to the other deletion mutants.

Figure 4:
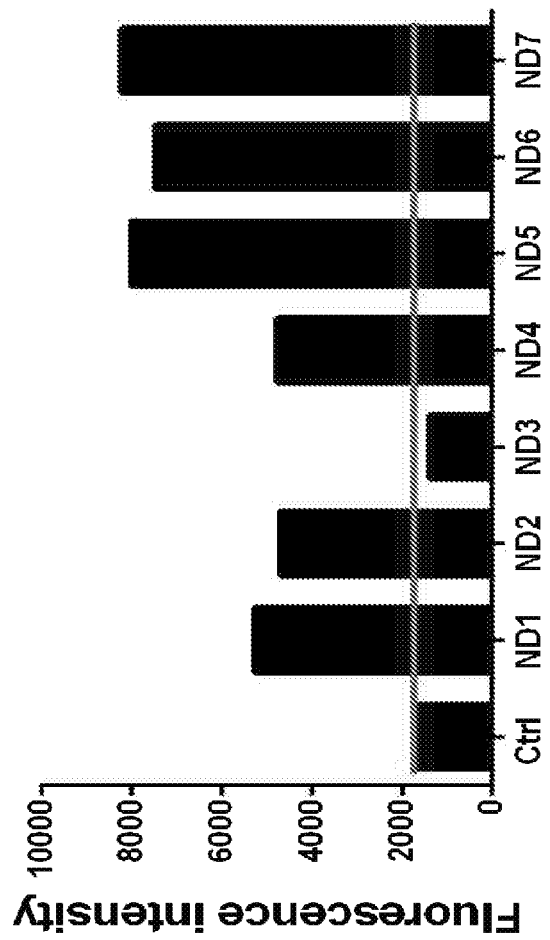
FIG. 4 provides binding of GBA to PGRN N-terminal deletion fragments by FRET assay. 293 EBNA cells were transfected with pDsRed-GBA encoding RFP-fused GBA and corresponding plasmids encoding various GFP-fused N-terminal deletions of PGRN, and the culture plate was scanned by SpectraMax® i3x Platform with GFP excitation wavelength (488 nm) and DsRed emission wavelength (588 nm).

N-terminal deletion mutants were then evaluated by FRET assay to further determine GBA binding to each mutant. The results are provided in FIG. 4. 293 EBNA cells were co-transfected with pDsRed-GBA, encoding RFP-fused GBA, and each corresponding plasmid encoding the various GFP-fused N-terminal deletions of PGRN. The culture plate was scanned by SpectraMax® i3x Platform with GFP excitation wavelength (488 nm) and DsRed emission wavelength (588 nm). The fluorescence intensity provides a quantitative indication of relative PGRN bound GBA. Mutants showed binding above control, with ND3 again showing the least binding, and mutants ND5, ND6 and ND7 showing the most significant binding.

To further evaluate GBA binding, PGRN serial deletions from the C-terminal end were constructed and evaluated. The scheme of constructs encoding serial GFP-tagged C-terminal deletion mutants of PGRN is depicted in FIG. 5A. The C-terminal derivative fragments of PGRN were as follows: CD1 (aa 1-521), CD2 (aa 1-444), CD3 (aa 1-376), CD4 (aa 1-284), CD5 (aa 1-209), CD6 (aa 1-127), and CD7 (aa 1-61), with PGRN full-length (FL) (aa 1-593) as control. Expression of GFP-tagged C-terminal deletion PGRN fragments was examined by immunoblotting with anti-GFP antibody to confirm expression of each C-terminal derivative (FIG. 5B).

Figure 6:
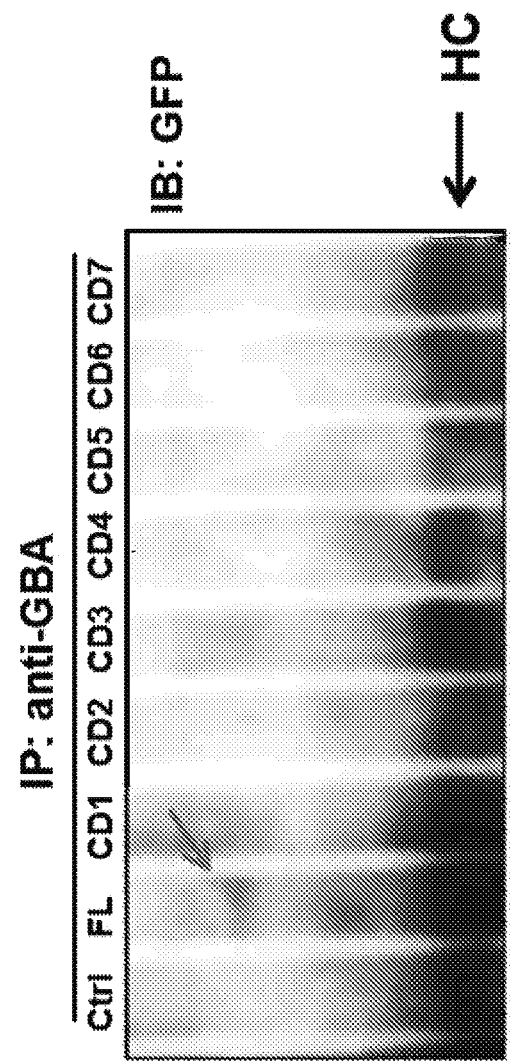
FIG. 6 provides binding of GBA to PGRN C-terminal serial deletions fragments by co-IP assay. 293 EBNA cells were transfected with pDsRed-GBA encoding RFP-fused GBA and corresponding plasmids encoding various GFP-fused C-terminal deletions of PGRN, as indicated, and the cell lysate were immunopricipated with GBA antibody. The complexes were probed with anti-GFP antibody. The positive band is indicated with an arrow. HC indicates IgG heavy chain.

Binding of GBA to the PGRN C-terminal serial deletions fragments was then assessed by co-IP assay (FIG. 6). 293 EBNA cells were transfected with pDsRed-GBA, encoding RFP-fused GBA, and corresponding plasmids encoding each of the various GFP-fused C-terminal deletions of PGRN. The cell lysates were immunoprecipitated with GBA antibody and the complexes probed with anti-GFP antibody. As shown in FIG. 6, only the full length (FL) PGRN bound GBA. None of the C-terminal deletions bound GBA.

Figure 7:
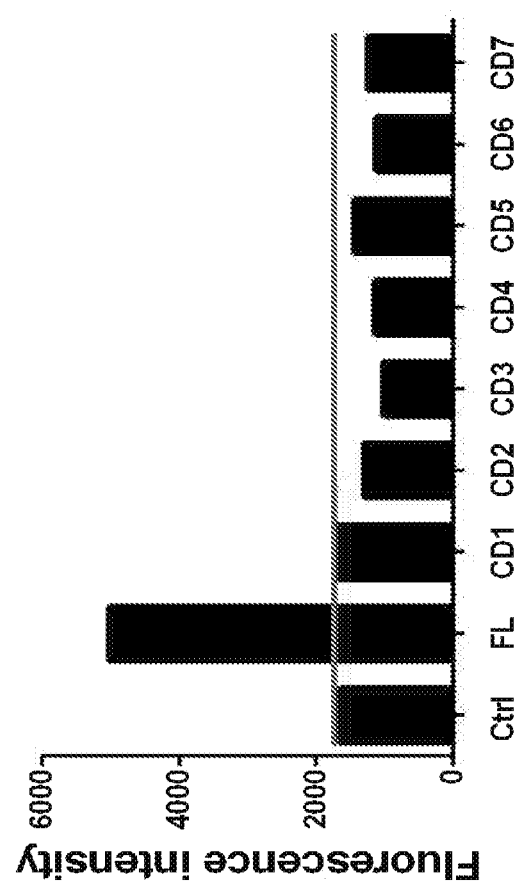
FIG. 7 provides binding of GBA to PGRN C-terminal serial deletions fragments by FRET assay. 293 EBNA cells were transfected with pDsRed-GBA encoding RFP-fused GBA and corresponding plasmids encoding various GFP-fused C-terminal deletions of PGRN and the culture plate was scanned by SpectraMax® i3x Platform with GFP excitation wavelength (488 nm) and DsRed emission wavelength (588 nm).

Binding of GBA to the PGRN C-terminal serial deletions fragments was further evaluated by FRET assay (FIG. 7). 293 EBNA cells were transfected with pDsRed-GBA, encoding RFP-fused GBA, and corresponding plasmids encoding each of the GFP-fused C-terminal deletions of PGRN. The culture plate was scanned by SpectraMax® i3x Platform with GFP excitation wavelength (488 nm) and DsRed emission wavelength (588 nm). The fluorescence intensity provides a quantitative indication of relative PGRN bound GBA. Confirming the co-immunoprecipitation results, only the full length PGRN showed GBA binding above background control.

The above studies demonstrated that the ND7 fragment, having amino acids 496-593 of PGRN, is sufficient for binding to GBA. The ND7 fragment was then evaluated in fibroblasts from lysosomal storage disease patients. Gaucher's disease patient fibroblasts were utilized to determine lysosomal trafficking in the presence of the ND7 N-terminal deletion derivative. Fibroblasts were challenged with lipid in combination with the PGRN ND7 fragment (0.4 µg/ml) for 24 hours. Fibroblasts from type 1 Gaucher's disease were transiently transfected with pEGFP control vector and ND7-EGFP vector. Forty-eight hours after transfection 50 nM LysoTracker® Deep Red was added in the cell culture supernatant for 1 hour, and live images were taken by Applied Precision Personal DV live-cell imaging system (NYU medical center core facility). Red color represents level of lysosome, and green color stand for cells expressing GFP-tagged proteins. The results (FIG. 8A) demonstrated that the ND7 fragment retains a therapeutic effect in Gaucher's disease cells, resulting in reduced lysosomal staining in the presence of ND7. Thus, according to our series C-terminal and N-terminal deletion mutants, a C-terminal 98 amino acid fragment (from aa 496-593, denoted ND7 and also denoted Pcgin) of PGRN, containing Grn E domain, was found to be both required and sufficient for binding to GBA/GCase.

Example 3

Figure 2:
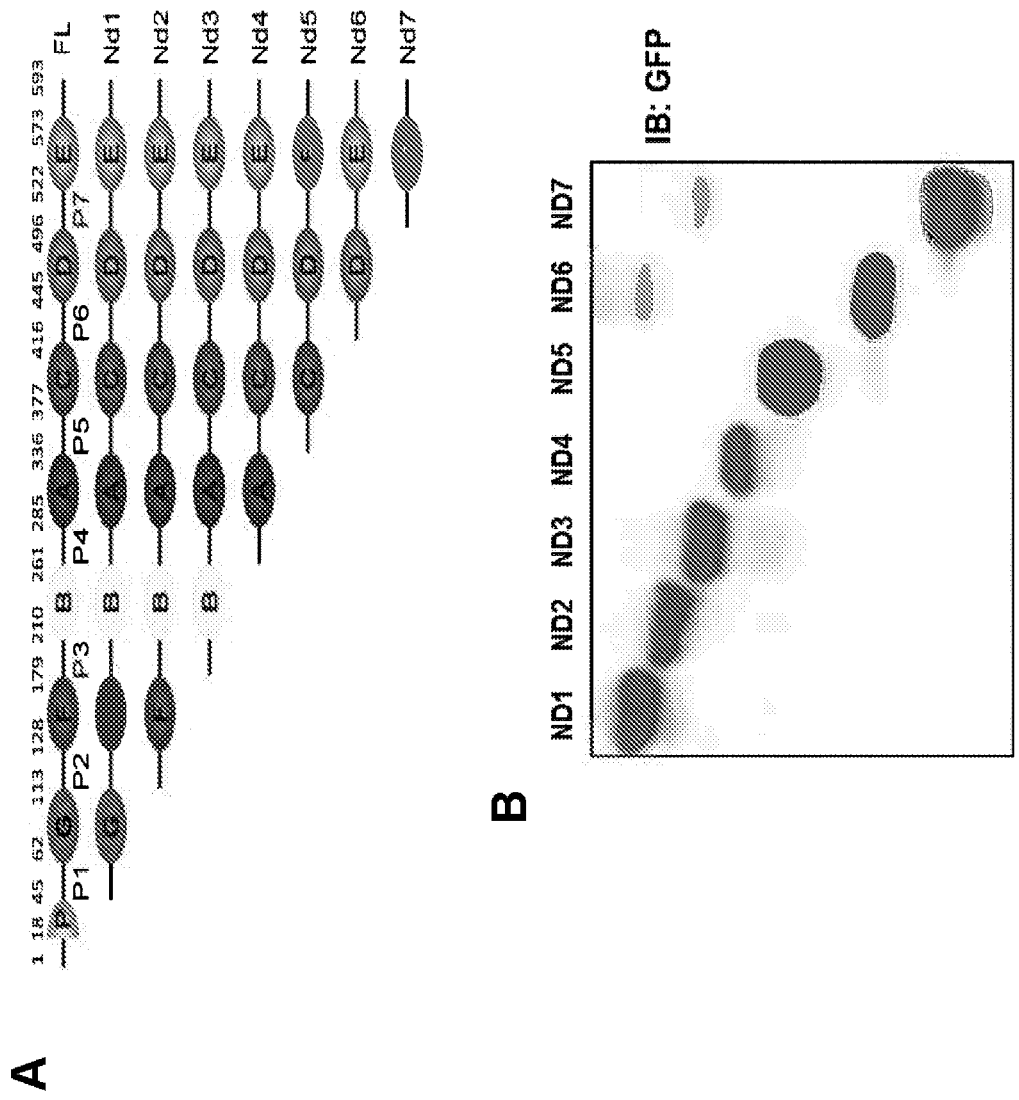
FIG. 2 depicts expression of PGRN serial deletions from the N-terminal end. (A) Scheme of constructs encoding serial GFP-tagged N-terminal deletion mutants of PGRN. The deletion mutants correspond to PGRN amino acid sequences as follows: ND1 (aa 45-593), ND2 (aa 113-593), ND3 (aa 179-593), ND4 (aa 261-593), ND5 (aa 336-593), ND6 (aa 416-593), and ND7 (aa 496-593). (B) Expression of GFP-tagged N-terminal deletion PGRN derivative fragments, examined by immunoblotting with anti-GFP antibody.

In order to further assess the minimal fragment that retains GCase/GBA-binding and functional activity of PGRN, we dissected the 98-aa fragment ND7/Pcgin with a series of fine-tune deletions. The deletion mutations constructed in ND7 and evaluated for GBA/GCase activity are depicted in FIG. 8A. Deletion of the linker on the left (the region of aa 540-573 corresponding to linker p7 of ND7)— this deletion mutant Δ496-522 (also denoted Δ1) retains the E granulin and C-terminal sequences as shown in FIG. 2 and corresponds to a PGRN fragment having amino acids 523-596 of PGRN—or deletion of the linker on the right of GrnE to generate deletion mutant Δ574-593 (also denoted Δ5), did not abolish binding to GCase and HSP70. However, deletion of 12 (aa523-534) and of 5 (aa535-539, RDNRQ) amino acid fragments completely abolished the binding activity to GCase and HSP70, respectively, indicating these 12 amino acids and the RDNRQ motif are responsible for binding to GCase and HSP70, respectively. Indeed, the RDNRQ motif fits the conserved HSP70 binding consensus sequence requirement (Almeida, S et al (2011) PloS One 6:e26454, doi:10.1371/journal.pone.0026454) (Dice, 1990). Another deletion mutant ΔQLL, deletion of the last three C-terminal amino acids in C-terminus of ND7, which have been shown to bind sortilin (Zheng Y et al (2011) PLoSOne 6(6):e21023, doi:10.1371/journal.pone.0021023) was also generated.

Figure 9A:
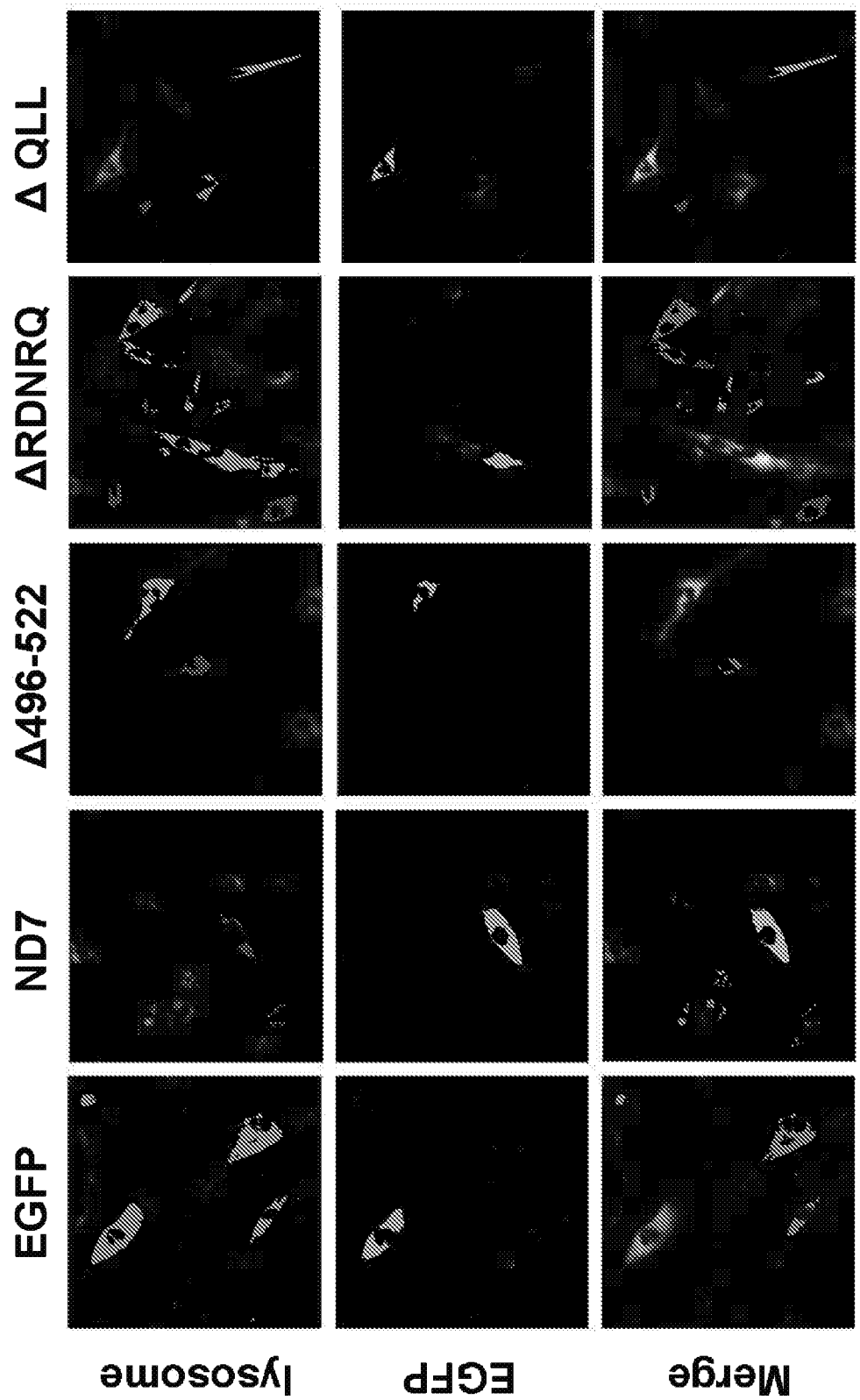
FIG. 9 depicts evaluation of the ND7 derivative fragment and various mutations of ND7 in Gaucher's disease fibroblasts. (A) Fibroblasts from type 1 Gaucher's disease were transient transfected with pEGFP control vector, ND7-EGFP vector, and three deletion mutations of ND7-EGFP vector, including Δ496-522, deletion of linker p7 of ND7 (please refer to FIG. 2 for information of p7), ΔRDNRQ, deletion of HSP70 binding site, and ΔQLL, deletion of last three amino acid in C-terminal of ND7, known to binding sortilin. Forty-eight hours after transfection 50 nM LysoTracker® Deep Red were added in the cell culture supernatant for 1 hour, and live images were taken by Applied Precision Personal DV live-cell imaging system (NYU medical center core facility). Red color represents level of lysosome, and green color stand for cells expressing GFP-tagged proteins. (B) Quantification analysis of the ND7 fragment and selected mutants of ND7 for effect on protein transport to the lysosome (therapeutic effect). Images from panel A were analyzed by ImageJ software. GFP+ and GFP− negative cells were selected, and lysosome content of each of the cells were determined by mean fluorescence intensity of LysoTracker®.

Fibroblasts from type 1 Gaucher's disease were transiently transfected with pEGFP control vector, ND7-EGFP vector, and the ND7 deletion mutations Δ496-522, ΔDNRQ, and ΔQLL. Forty-eight hours after transfection 50 nM LysoTracker® Deep Red were added in the cell culture supernatant for 1 hour, and live images were taken by Applied Precision Personal DV live-cell imaging system (NYU medical center core facility). The results indicate that all of Δ496-522, ΔDNRQ, and ΔQLL deletion mutants lose therapeutic activity (FIG. 9A).

Figure 9B:
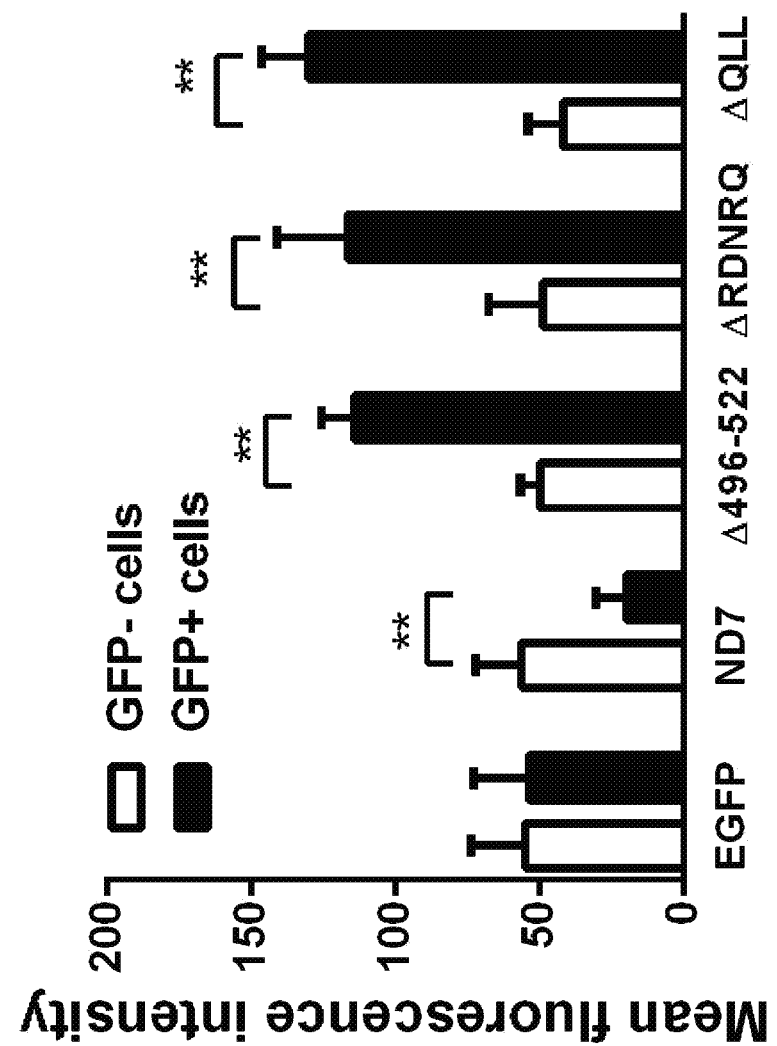

The GBA therapeutic effect of ND7 and certain ND7 deletion mutants was evaluated quantitatively (FIG. 9B). Images from panel FIG. 9A were analyzed by ImageJ software. GFP+ and GFP-negative cells were selected, and the lysosome content of each of the cells were determined by mean fluorescence intensity of LysoTracker® (Kirkegaard, T et al. (2010) *Nature* 463, 549-553). Each of the three ND7 deletion mutants evaluated, Δ496-522, ΔDNRQ, and ΔQLL, demonstrated elevated fluorescence in the lysosome versus the control. ND7, however, showed significantly reduced fluorescence in the lysosome indicating significantly reduced lysosomal storage with administration of ND7 PGRN, but each of the three ND7 mutants totally lost therapeutic effects. Actually these mutants led to even severer phenotypes compared to the control, suggesting that these mutants may act as the dominant negatives of the endogenous PGRN.

The above results demonstrate that amino acids 496-593 of PGRN, corresponding to denoted PGRN fragment ND7, are sufficient for GBA binding and also sufficient to modify lysosomal trafficking effects in lysosomal storage disease cells. The ND7 fragment encompasses predicted HSP70 and sortilin binding sites of PGRN. Deletion of these sites abolishes the lysosome effect. However, deletion of N-terminal ND7 amino acids 496-522, which corresponds to the linker P7 also abolishes the lysosome effect. These results are distinct from binding studies such as for sortilin, wherein Zheng et al have shown that deletion of the 3 C-terminal residues of PGRN abolish sortilin binding, however, having the last six C-terminal amino acids are sufficient for sortilin binding to PGRN. Also, assessment of proteolytic conversion of proepithelin (PGRN) to epithelins (granulins) by Zhu et al, including elastase cleavage sites showed cleavage at the second V (valine) in the sequence VGVKDVECGEGHF of human PGRN to generate a fragment corresponding 517-593, which is distinct from the active novel ND7 fragment of amino acids 496-593 (Zhu, J et al (2002) *Cell* 111(6):867-878). Thus, the ND7 fragment is distinct from proteolytic fragment(s) which may be generated in vivo.

The amino acids necessary and sufficient for GBA binding by PGRN encompass ND7 and amino acids 496-593. ND7 provides a novel and unique PGRN derivative with application for lysosomal storage diseases, particularly including Gaucher's disease. Taken together, these results suggest that the c-terminal 98 amino acid fragment also denoted ND7 appears to be the "minimal" molecule that retains GBA/GCase-binding and functional activities. This molecule is referred to as Pcgin (PGRN C-terminus for GCase Interaction). The structure and amino acid sequence of Pcgin are shown in FIG. 8C.

Figure 10:
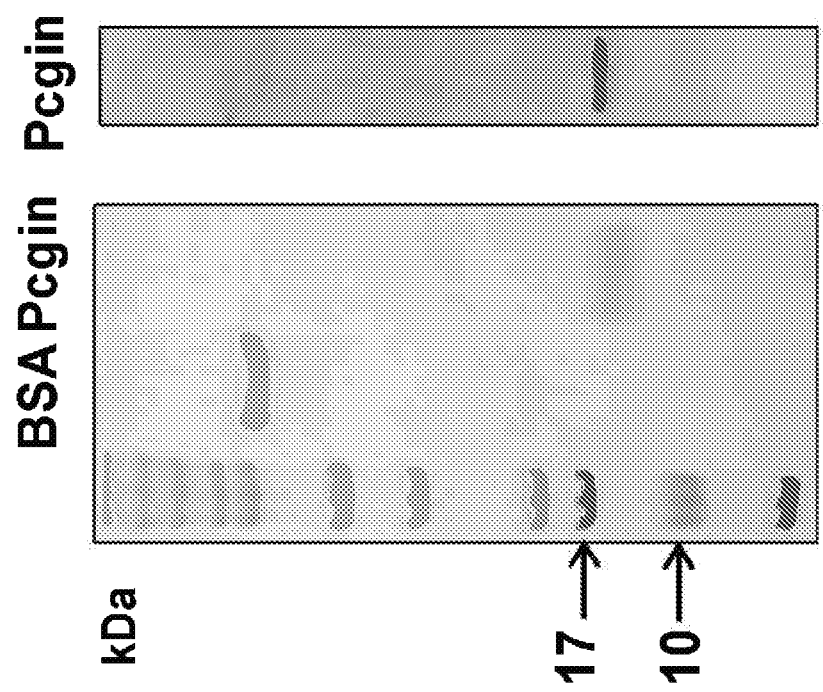
FIG. 10 depicts expression and characterization of recombinant Pcgin/ND7 fragment of PGRN. The purified Pcgin was analyzed by Coomassie blue staining (left) and Western blotting with anti-His antibody (right).
Figure 11:
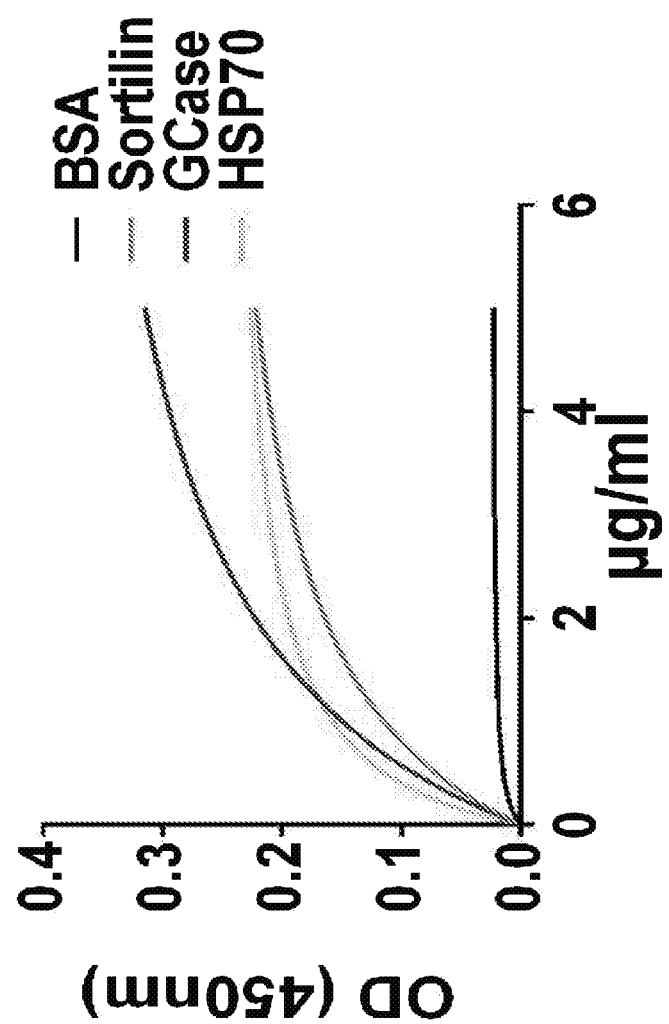
FIG. 11 shows recombinant Pcgin directly binds to GCase and HSP70 (Solid phase binding). Pcgin was coated on a 96-well plate and incubated with biotin-labeled GCase, HSP70, and Sortilin (serving as a positive control) respectively. The direct binding was detected by ELISA-based method.

Pcgin was then expressed in bacteria and purified as a His-tagged protein. The purity was examined by Coomassie Blue staining and confirmed by Western blotting with His probe (FIG. 10). Using a solid phase binding assay (FIG. 11) we found that recombinant Pcgin directly bound to GCase, HSP70 and sortilin (known to bind to the last three amino acids QLL of PGRN and serving as a positive control) (Zheng et al., 2011). Although Pcgin retained GCase and HSP70 binding activity of PGRN, it lacked PGRN's oncogenic activity, including PGRN-activated oncogenic signaling and cell proliferation (data not shown).

Example 4

Evaluation of PGRN ND7/Pcgin in Animal Models and in Disease Cells

Pcgin (ND7 PGRN fragment, amino acids 496-593) was evaluated for a therapeutic effect in vivo in an animal model. PGRN KO mice, a chronic lung inflammation model which demonstrates Gaucher's disease phenotype as described herein and in PCT US2010/014364 filed Feb. 4, 2015 and U.S. Ser. No. 61/935,541 filed Feb. 4, 2014, was utilized to further determine the therapeutic effect of ND7. PGRN KO mice are hosted in the animal facility of New York University as previously described_ENREF_1 (Tang, W. et al. (2011) *Science* 332, 478-484; Yin, F. et al (2010) *J Exp Med* 207(1):117-128).

Figure 12:
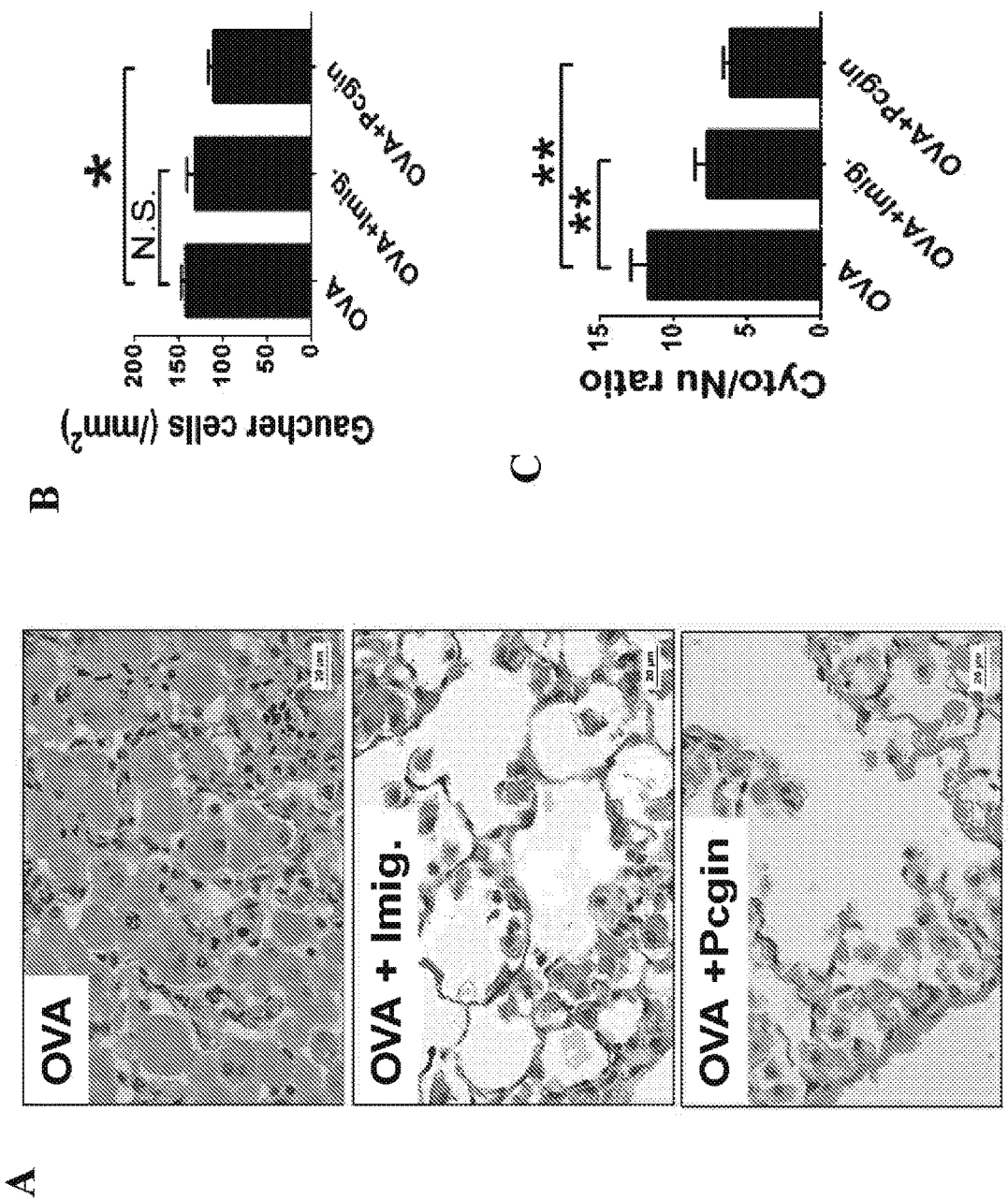
FIG. 12 demonstrates that Pcgin is therapeutic against GD phenotype in OVA-challenged PGRN KO mice. (A) GD phenotype was induced in PGRN KO mice, and mice were treated with either Pcgin or Imiglucerase (Imig. serving as a positive control) (n=6 per group). Lung tissues were examined by H&E staining. Gaucher cell number (B) and Gaucher cell sizes (C) were significantly reduced after Pcgin treatment. One-way ANOVA was used to compare means among multiple groups (Data are represented as mean±SEM, *p<0.05; **p<0.01; two sided).

Gaucher's disease (GD) phenotype was induced by OVA challenge in 8-week-old PGRN deficient mice as described above (n=6 per group). Pcgin (4 mg/kg/week) was I.P injected starting from the first week of intranasal challenge and continuing for 5 weeks, at which point, the mice were sacrificed. Another group was injected with imiglucerase as a positive control. In the untreated group, mice developed a severe GD phenotype and large Gaucher cells occupied lung tissues. However, histology of lung tissue revealed dramatic improvement in the Pcgin treated group (FIG. 12A). Quantification data shows that Pcgin significantly reduced both the number and size of Gaucher cells, while imiglucerase only reduced Gaucher cell size (FIG. 12B, 12C). These results demonstrate that Pcgin is a promising drug candidate for treating Gaucher disease.

Figure 13:
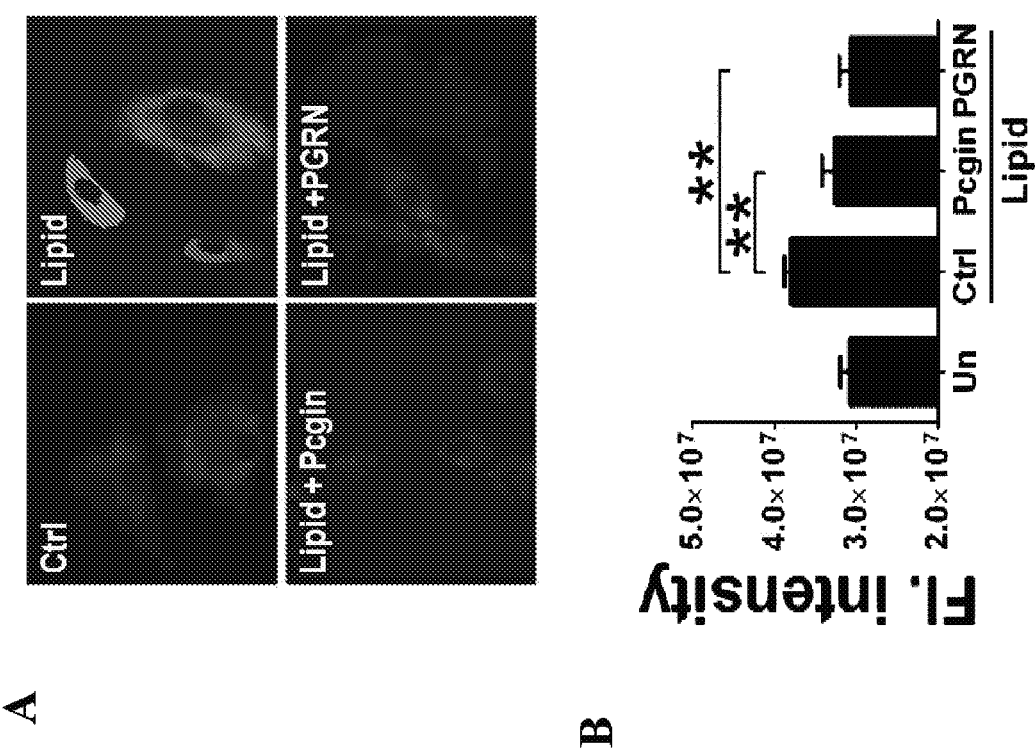
FIG. 13. Pcgin reduces lysosome storage in type 2 GD fibroblasts (D409H). (A) Fibroblasts from GD patients were stimulated with lipid, or lipid plus Pcgin (0.4 µg/ml) or plus PGRN (0.4 µg/ml). The lysosomal storage was measured by LysoTracker staining. (B) depicts quantification of (A). Ten images per sample were taken by fluorescence microscope, and fluorescence (FL) intensity was measured by Image J software, and therapeutic effects were determined by statistical analysis.
Figure 14:
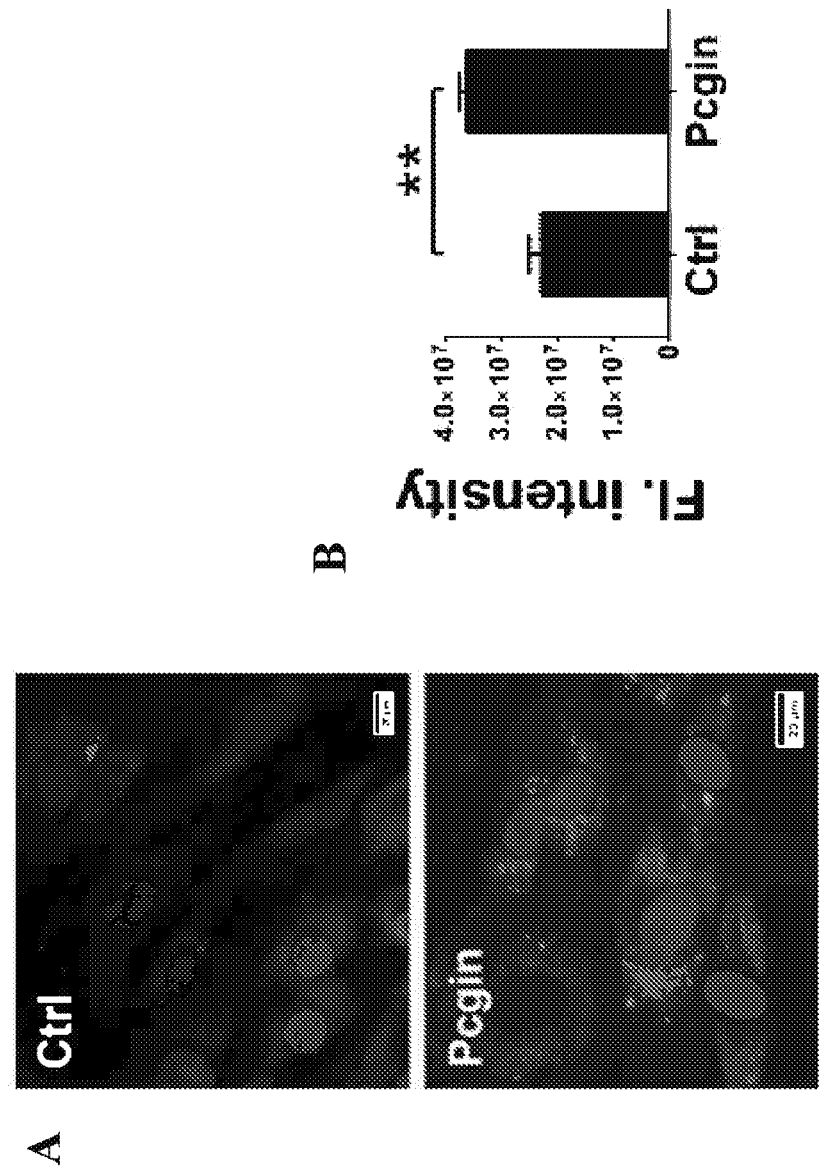
FIG. 14 shows Pcgin enhances lysosomal localization of mutant GBA1 (N370S). (A) Type 1 GD fibroblasts were treated with Pcgin (0.4 µg/ml) for 24 hours, and the lysosomal GCase was detected with its specific fluorescence probe MDW933. (B) depicts quantification of (A).

We next examined the therapeutic effects of recombinant Pcgin in GD fibroblasts. Similar to PGRN, recombinant Pcgin significantly reduced lysosome content in fibroblasts from type 2 GD patients (D409H) (FIG. 13). In addition, Pcgin also effectively led to the lysosomal localization of mutant GBA1 (N370S) in type 1 GD fibroblasts, visualized by MDW933, a specific probe for lysosomal GCase (Aerts et al., 2011; Gaspar et al., 2014; Witte et al., 2010) ENREF_29 (FIG. 14).

Figure 15:
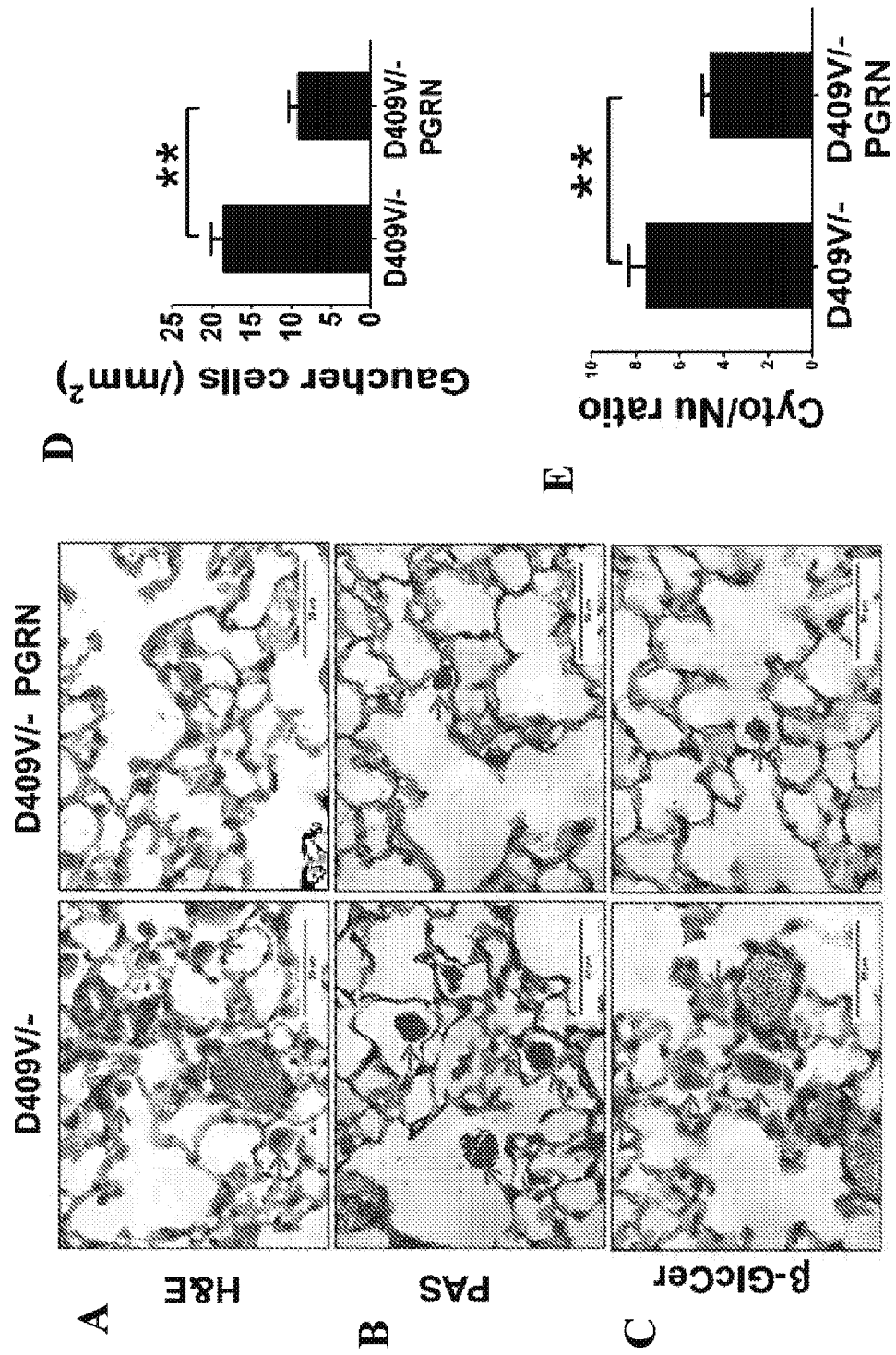
FIG. 15 shows rPGRN ameliorates GD phenotype in D409V/− mouse model. Five week-old D409V/− mice were injected with PBS or rPGRN (4 mg/kg/week) for 4 weeks (n=5 per group). The mice were sacrificed and lung tissues were collected for histological analyses. (A) H&E staining, (B) PAS staining, and (C) immunohistochemistry staining of β-GlcCer, (D) Gaucher cells number, (E) Gaucher cells size.
Figure 16:
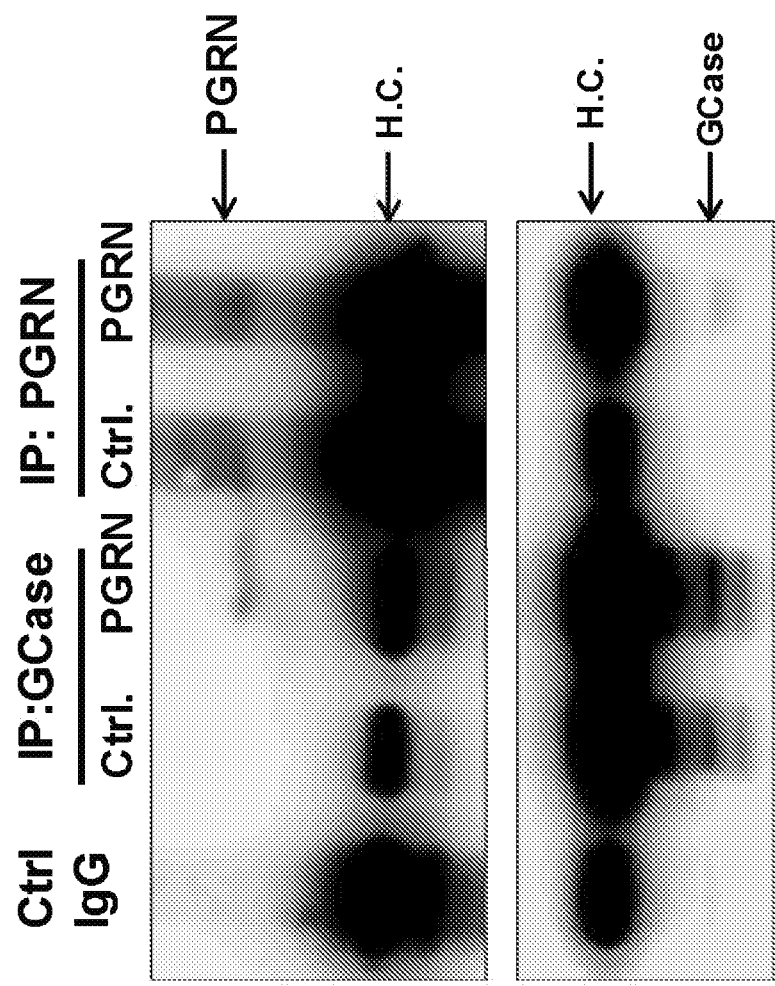
FIG. 16 shows rPGRN treatment leads to detectable interaction between PGRN and GCase in D409V/null mice. Spleen lyses from D409V/null mice with or without rPGRN treatment were co-immunoprecipitated with antibodies against GCase or PGRN, and probed with PGRN and GCase antibodies, respectively.

In a separate experiment, the therapeutic effect of rPGRN in GD was further demonstrated with an established specific GD animal model. We took advantage of D409V/− GD mice, a GD model generated by deleting one allele of the Gba1 gene, with the other allele carrying a D409V point mutation (Barnes et al., 2014). This mutated GCase is unstable and is degraded very quickly (Liou et al., 2006), and these Gba1 mutant mice spontaneously develop Gaucher cells at around 8 weeks. 5-weeks-old D409V/− mice were injected with rPGRN (4 mg/kg/week) for 4 weeks and then sacrificed for histological and β-GlcCer analyses. rPGRN administration significantly reduced pathological severity (FIG. 15A) as well as the accumulation of glycolipids (FIG. 15B), including β-GlcCer (FIG. 15C). The number and the size of Gaucher cells were significantly reduced followed rPGRN treatment (FIG. 15D, 15E). In addition, rPGRN treatment, which stabilized and increased the levels of GCase, led to detectability of the interaction between mutant GCase and PGRN (FIG. 16).

Figure 17:
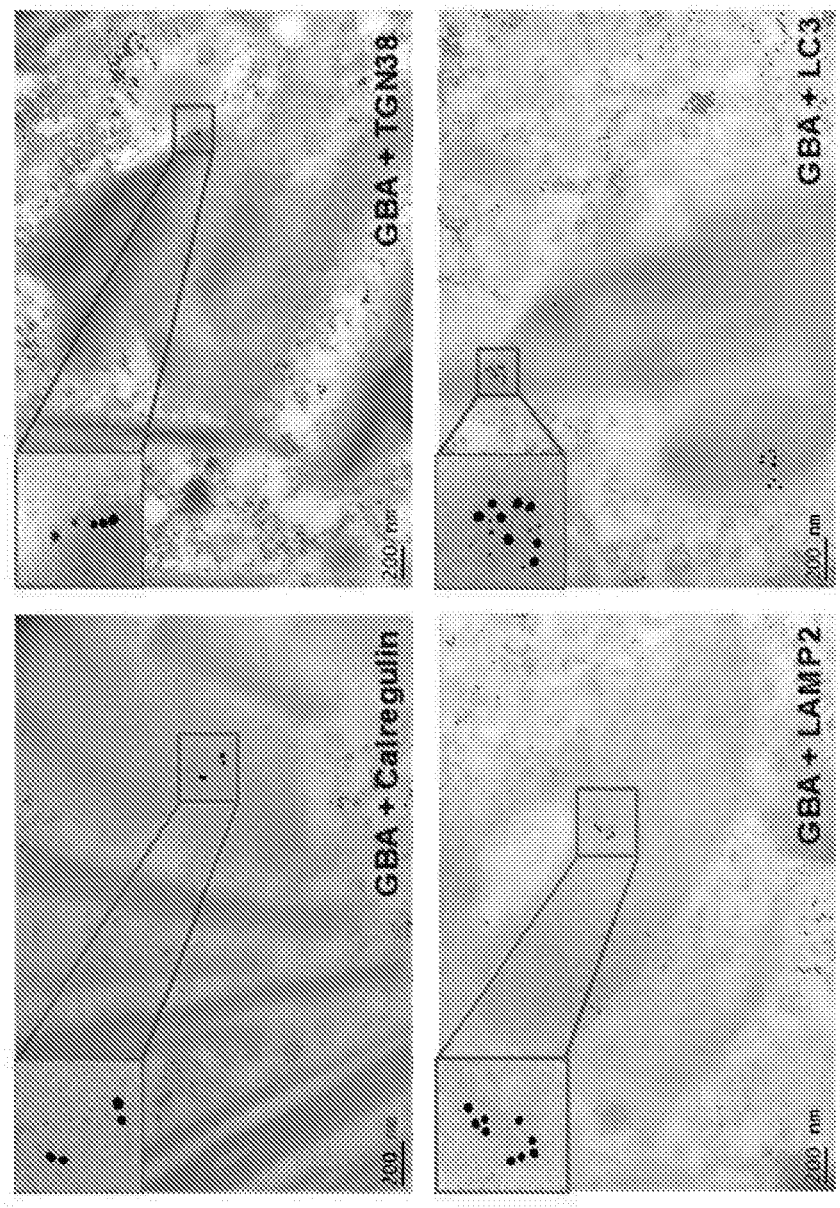
FIG. 17 depicts co-immunogold staining of GBA and organelle markers. Lung tissue from PGRN KO mice after OVA challenge were co-immunogold stained with GBA (18 nm particle) and different organelle markers (5 nm particle) including ER marker Calregulin, trans-Golgi marker TGN38, lysosome marker LAMP2 and autophagy marker LC3. These samples were imaged under EM (40,000×).

To understand the nature of GCase aggregation, we also performed co-immunogold staining of GCase with various organelle markers, including ER, trans-Golgi network, lysosome, and autophagy markers. GCase was found to be specifically co-localized with the autophagy marker LC3 in aggregates (FIG. 17) suggesting that GCase aggregates, caused by either GCase mutation or PGRN deficiency, may enter the autophagy/lysosome pathway, and that the autophagy/lysosome pathway may be involved in PGRN regulation of GCase lysosomal delivery.

REFERENCES

Aerts, J. M., Kallemeijn, W. W., Wegdam, W., Joao Ferraz, M., van Breemen, M. J., Dekker, N., Kramer, G., Poorthuis, B. J., Groener, J. E., Cox-Brinkman, J., et al. (2011). Biomarkers in the diagnosis of lysosomal storage disorders: proteins, lipids, and inhibodies. Journal of inherited metabolic disease 34, 605-619.

Barnes, S., Xu, Y. H., Zhang, W., Liou, B., Setchell, K. D., Bao, L., Grabowski, G. A., and Sun, Y. (2014). Ubiquitous transgene expression of the glucosylceramide-synthesizing enzyme accelerates glucosylceramide accumulation and storage cells in a Gaucher disease mouse model. PloS one 9, e116023.

Bateman, A., and Bennett, H. P. (2009). The granulin gene family: from cancer to dementia. BioEssays: news and reviews in molecular, cellular and developmental biology 31, 1245-1254.

Dice, J. F. (1990). Peptide sequences that target cytosolic proteins for lysosomal proteolysis. Trends in biochemical sciences 15, 305-309.

Gaspar, P., Kallemeijn, W. W., Strijland, A., Scheij, S., Van Eijk, M., Aten, J., Overkleeft, H. S., Balreira, A., Zunke, F., Schwake, M., et al. (2014). Action myoclonus-renal failure syndrome: diagnostic applications of activity-based probes and lipid analysis. Journal of lipid research 55, 138-145.

He, Z., and Bateman, A. (1999). Progranulin gene expression regulates epithelial cell growth and promotes tumor growth in vivo. Cancer Res 59, 3222-3229.

He, Z., Ismail, A., Kriazhev, L., Sadvakassova, G., and Bateman, A. (2002). Progranulin (PC-cell-derived growth factor/acrogranin) regulates invasion and cell survival. Cancer Res 62, 5590-5596.

Liou, B., Kazimierczuk, A., Zhang, M., Scott, C. R., Hegde, R. S., and Grabowski, G. A. (2006). Analyses of variant acid beta-glucosidases: effects of Gaucher disease mutations. The Journal of biological chemistry 281, 4242-4253.

Witte, M. D., Kallemeijn, W. W., Aten, J., Li, K. Y., Strijland, A., Donker-Koopman, W. E., van den Nieuwendijk, A. M., Bleijlevens, B., Kramer, G., Florea, B. I., et al. (2010). Ultrasensitive in situ visualization of active glucocerebrosidase molecules. Nature chemical biology 6, 907-913.

Zheng, Y., Brady, O. A., Meng, P. S., Mao, Y., and Hu, F. (2011). C-terminus of progranulin interacts with the beta-propeller region of sortilin to regulate progranulin trafficking. PloS one 6, e21023.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A composition comprising a fragment of progranulin (PGRN) consisting of: SEQ ID NO:4; a first active variant wherein one or more amino acids in SEQ NO:4 is substituted, wherein the first variant is at least 90% amino acid sequence identical to SEQ ID NO:4 and comprising EGHFCHDNQTCC (SEQ ID NO:7), and wherein the first variant binds glucocerebrosidase (GBA/GCase); or a second active variant wherein one or more amino acids in SEQ ID NO:4 is substituted, wherein the second variant is at least 90% amino acid sequence identical to SEQ ID NO:4 and comprising RDNRQ (SEQ ID NO:8) and QLL, and wherein the second variant binds HSP70 and sortilin.

2. The composition of claim 1 wherein the PGRN fragment consists of SEQ ID NO: 4.

3. The composition of claim 1 wherein the PGRN fragment is the first active variant wherein one or more amino acids in SEQ ID NO:4 is substituted with a conservative amino acid and wherein the first variant binds GBA/GCase.

4. The composition of claim 1 wherein the PGRN fragment is the first active variant wherein one or more amino acids in SEQ ID NO:4 are replaced with one or more corresponding mouse amino acids of SEQ ID NO:6 and wherein the first variant binds GBA/GCase.

5. The composition of claim 1 further comprising an enzyme replacement therapy agent or substrate reduction therapy agent for a lysosomal storage disease.

6. The composition of claim 5 further comprising one or more of glucocerebrosidase, α-galactosidase, β-galactosidase, β-hexosaminidase and sphingomyelinase.

7. The composition of claim 1, further comprising glucocerebrosidase (GBA/GCase) for treatment or alleviation of Gaucher's Disease.

8. The composition of claim 1, further comprising β-hexosaminidase A for treatment or alleviation of Tay-Sachs disease.

9. The composition of claim 1, further comprising one or more molecular chaperone or lysosomal delivery protein.

10. The composition of claim 9 wherein the molecular chaperone or lysosomal delivery protein is HSP70.

11. The composition of claim 1 which is a pharmaceutical composition and further comprises a pharmaceutically acceptable carrier, vehicle, diluent or excipient.

12. A method for facilitating lysosomal delivery of a protein or enzyme in an animal comprising administering to said animal the composition of claim 1.

13. A method for facilitating delivery of glucocerebrosidase (GBA/GCase) in a patient having Gaucher's Disease comprising administering the composition of claim 1 and GBA/GCase to said patient.

14. A method for treating or alleviating a lysosomal storage disease in an animal comprising administering to said animal the composition of claim 1.

15. The method of claim 14 comprising additionally administering one or more lysosomal enzyme which is reduced, absent, mutated or altered in the lysosomal storage disease.

16. The method of claim 14 wherein the lysosomal storage disease is selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease.

17. The method of claim 14 comprising additionally administering the lysosomal enzyme glucocerebrosidase (GBA/GCase) or an active fragment or recombinant form thereof for treating or alleviating Gaucher's Disease.

18. An isolated polypeptide fragment of PGRN consisting of: SEQ ID NO:4; a first active variant wherein one or more amino acids in SEQ ID NO:4 is substituted, wherein the first variant is at least 90% amino acid identical to SEQ ID NO:4 and comprising EGHFCHDNQTCC (SEQ ID NO:7), and wherein the first variant binds glucocerebrosidase GBA/GCase; or a second active variant wherein one or more amino acids in SEQ ID NO:4 is substituted, wherein the second variant is at least 90% amino acid sequence identical to SEQ ID NO:4 and comprising RDNRQ (SEQ ID NO:8) and QLL, and wherein the second variant binds HSP70 and sortilin.

19. The isolated polypeptide fragment of PGRN of claim 18 which is the first active variant wherein one or more amino acids in SEQ ID NO:4 is substituted with a conservative amino acid and wherein the first variant binds GBA/GCase.

20. The isolated polypeptide fragment of PGRN of claim 18 which is the first active variant wherein one or more amino acids in SEQ ID NO:4 are replaced with one or more corresponding mouse amino acids of SEQ ID NO:6 and wherein the first variant binds GBA/GCase.

21. The isolated polypeptide fragment of PGRN of claim 18 which is the second active variant wherein one or more amino acids in SEQ ID NO:4 is substituted with a conservative amino acid and wherein the second variant binds HSP70 and sortilin.

22. The isolated polypeptide fragment of PGRN of claim 18 which is the second active variant wherein one or more amino acids in SEQ ID NO:4 are replaced with one or more corresponding mouse amino acids of SEQ ID NO:6 and wherein the second variant binds HSP70 and sortilin.

23. The composition of claim 1 wherein the PGRN fragment is the second active variant wherein one or more amino acids in SEQ ID NO:4 is substituted with a conservative amino acid and wherein the second variant binds HSP70 and sortilin.

24. The composition of claim 1 wherein the PGRN fragment is the second active variant wherein one or more amino acids in SEQ D NO:4 are replaced with one or more corresponding mouse amino acids of SEQ ID NO:6 and wherein the second variant binds HSP70 and sortilin.

* * * * *

SEQUENCE LISTING

```
<160> NUMBER OF SEQ ID NOS: 8

<210> SEQ ID NO 1
<211> LENGTH: 53
<212> TYPE: PRT
<213> ORGANISM: artificial sequence
<220> FEATURE:
<223> OTHER INFORMATION: cysteine-rich motif
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: variant
<222> LOCATION: (7)..(7)
<223> OTHER INFORMATION: Xaa can be any amino acid or no amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (16)..(23)
<223> OTHER INFORMATION: Xaa can be any naturally occurring amino acid
<220> FEATURE:
<221> NAME/KEY: misc_feature
<222> LOCATION: (26)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (42)..(45)
<223> OTHER INFORMATION: Xaa can be any naturally occurring amino acid
<220> FEATURE:
<221> NAME/KEY: misc_feature
```

```
<222> LOCATION: (47)..(51)
<223> OTHER INFORMATION: Xaa can be any naturally occurring amino acid
<220> FEATURE:
<221> NAME/KEY: variant
<222> LOCATION: (52)..(52)
<223> OTHER INFORMATION: Xaa can be any amino acid or no amino acid

<400> SEQUENCE: 1

Cys Xaa Xaa Xaa Xaa Xaa Cys Xaa Xaa Xaa Xaa Cys Cys Xaa
 1               5                  10                  15

Xaa Xaa Xaa Xaa Xaa Xaa Cys Cys Xaa Xaa Xaa Xaa Xaa Cys
            20                  25                  30

Cys Xaa Asp Xaa Xaa His Cys Cys Pro Xaa Xaa Xaa Xaa Cys Xaa Xaa
            35                  40                  45

Xaa Xaa Xaa Xaa Cys
        50

<210> SEQ ID NO 2
<211> LENGTH: 593
<212> TYPE: PRT
<213> ORGANISM: Homo sapiens

<400> SEQUENCE: 2

Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270
```

Lys Leu Pro Ala His Thr Val Gly Asp Val Lys Cys Asp Met Glu Val
                275                 280                 285

Ser Cys Pro Asp Gly Tyr Thr Cys Cys Arg Leu Gln Ser Gly Ala Trp
290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
                340                 345                 350

Ser Leu Pro Asp Pro Gln Ala Leu Lys Arg Asp Val Pro Cys Asp Asn
                355                 360                 365

Val Ser Ser Cys Pro Ser Ser Asp Thr Cys Cys Gln Leu Thr Ser Gly
                370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
                420                 425                 430

Arg Ala Ser Leu Ser His Pro Arg Asp Ile Gly Cys Asp Gln His Thr
                435                 440                 445

Ser Cys Pro Val Gly Gln Thr Cys Cys Pro Ser Leu Gly Gly Ser Trp
                450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
                500                 505                 510

His Val Gly Val Lys Asp Val Glu Cys Gly Glu Gly His Phe Cys His
                515                 520                 525

Asp Asn Gln Thr Cys Cys Arg Asp Asn Arg Gln Gly Trp Ala Cys Cys
                530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
                580                 585                 590

Leu

<210> SEQ ID NO 3
<211> LENGTH: 588
<212> TYPE: PRT
<213> ORGANISM: Mus musculus

<400> SEQUENCE: 3

Met Trp Ile Leu Val Ser Trp Leu Ala Leu Val Ala Arg Leu Val Ala
1               5                   10                  15

Gly Thr Gln Cys Pro Asp Gly Gln Phe Cys Pro Val Ala Cys Cys Leu
                20                  25                  30

Asp Gln Gly Gly Ala Asn Tyr Ser Cys Cys Asn Pro Leu Leu Asp Thr
                35                  40                  45

```
Trp Pro Ile Ile Thr Ser Arg Arg Leu Asp Gly Ser Cys Gln Ile Arg
    50                  55                  60
Asp His Cys Pro Asp Gly Tyr Ser Cys Leu Leu Thr Val Ser Gly Thr
65                  70                  75                  80
Ser Ser Cys Cys Pro Phe Ser Glu Gly Val Ser Cys Asp Asp Gly Gln
                85                  90                  95
His Cys Cys Pro Arg Gly Phe His Cys Ser Ala Asp Gly Lys Ser Cys
            100                 105                 110
Ser Gln Ile Ser Asp Ser Leu Leu Gly Ala Val Gln Cys Pro Gly Ser
        115                 120                 125
Gln Phe Glu Cys Pro Asp Ser Ala Thr Cys Cys Ile Met Ile Asp Gly
    130                 135                 140
Ser Trp Gly Cys Cys Pro Met Pro Gln Ala Ser Cys Cys Glu Asp Arg
145                 150                 155                 160
Val His Cys Cys Pro His Gly Ala Ser Cys Asp Leu Val His Thr Arg
                165                 170                 175
Cys Ile Ser Pro Thr Gly Thr His Pro Leu Leu Lys Lys Phe Pro Ala
            180                 185                 190
Gln Arg Thr Asn Arg Ala Val Ala Ser Phe Ser Val Val Cys Pro Asp
        195                 200                 205
Ala Lys Thr Gln Cys Pro Asp Asp Ser Thr Cys Cys Glu Leu Pro Thr
    210                 215                 220
Gly Lys Tyr Gly Cys Cys Pro Met Pro Asn Ala Ile Cys Cys Ser Asp
225                 230                 235                 240
His Leu His Cys Cys Pro Gln Asp Thr Val Cys Asp Leu Ile Gln Ser
                245                 250                 255
Lys Cys Ile Ser Lys Asp Tyr Thr Thr Asp Leu Met Thr Lys Leu Pro
            260                 265                 270
Gly Tyr Pro Val Asn Glu Val Lys Cys Asp Leu Glu Val Ser Cys Pro
        275                 280                 285
Asp Gly Tyr Thr Cys Cys Arg Leu Asn Thr Gly Ala Trp Gly Cys Cys
    290                 295                 300
Pro Phe Thr Lys Ala Val Cys Cys Glu Asp His Ile His Cys Cys Pro
305                 310                 315                 320
Ala Gly Phe Gln Cys His Thr Glu Thr Gly Thr Cys Glu Leu Gly Val
                325                 330                 335
Leu Gln Val Pro Trp Met Lys Lys Val Thr Ala Ser Leu Ser Leu Pro
            340                 345                 350
Asp Pro Gln Ile Leu Lys Asn Asp Val Pro Cys Asp Asp Phe Ser Ser
        355                 360                 365
Cys Pro Ser Asn Asn Thr Cys Cys Arg Leu Ser Ser Gly Asp Trp Gly
    370                 375                 380
Cys Cys Pro Met Pro Glu Ala Val Cys Cys Leu Asp His Gln His Cys
385                 390                 395                 400
Cys Pro Gln Gly Phe Lys Cys Met Asp Glu Gly Tyr Cys Gln Lys Gly
                405                 410                 415
Asp Arg Met Val Ala Gly Leu Glu Lys Met Pro Val Arg Gln Thr Thr
            420                 425                 430
Leu Leu Gln His Gly Asp Ile Gly Cys Asp Gln His Thr Ser Cys Pro
        435                 440                 445
Val Gly Gln Thr Cys Cys Pro Ser Leu Lys Gly Ser Trp Ala Cys Cys
    450                 455                 460
```

-continued

```
Gln Leu Pro His Ala Val Cys Cys Glu Asp Arg Gln His Cys Cys Pro
465                 470                 475                 480

Ala Gly Tyr Thr Cys Asn Val Lys Ala Arg Thr Cys Glu Lys Asp Ala
                485                 490                 495

Gly Ser Val Gln Pro Ser Met Asp Leu Thr Phe Gly Ser Lys Val Gly
            500                 505                 510

Asn Val Glu Cys Gly Ala Gly His Phe Cys His Asp Asn Gln Ser Cys
        515                 520                 525

Cys Lys Asp Ser Gln Gly Gly Trp Ala Cys Cys Pro Tyr Val Lys Gly
    530                 535                 540

Val Cys Cys Arg Asp Gly Arg His Cys Cys Pro Ile Gly Phe His Cys
545                 550                 555                 560

Ser Ala Lys Gly Thr Lys Cys Leu Arg Lys Lys Thr Pro Arg Trp Asp
                565                 570                 575

Ile Leu Leu Arg Asp Pro Ala Pro Arg Pro Leu Leu
            580                 585
```

<210> SEQ ID NO 4
<211> LENGTH: 98
<212> TYPE: PRT
<213> ORGANISM: Homo sapiens

<400> SEQUENCE: 4

```
Glu Lys Glu Val Val Ser Ala Gln Pro Ala Thr Phe Leu Ala Arg Ser
1               5                   10                  15

Pro His Val Gly Val Lys Asp Val Glu Cys Gly Glu Gly His Phe Cys
            20                  25                  30

His Asp Asn Gln Thr Cys Cys Arg Asp Asn Arg Gln Gly Trp Ala Cys
        35                  40                  45

Cys Pro Tyr Arg Gln Gly Val Cys Cys Ala Asp Arg Arg His Cys Cys
    50                  55                  60

Pro Ala Gly Phe Arg Cys Ala Ala Arg Gly Thr Lys Cys Leu Arg Arg
65                  70                  75                  80

Glu Ala Pro Arg Trp Asp Ala Pro Leu Arg Asp Pro Ala Leu Arg Gln
                85                  90                  95

Leu Leu
```

<210> SEQ ID NO 5
<211> LENGTH: 158
<212> TYPE: PRT
<213> ORGANISM: Artificial sequence
<220> FEATURE:
<223> OTHER INFORMATION: atsttrin

<400> SEQUENCE: 5

```
Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
        35                  40                  45

Ala Leu Ser Ser Ser Ala Ser Ser Lys Glu Asn Ala Thr Thr Asp Leu
    50                  55                  60

Leu Thr Lys Leu Pro Ala His Thr Val Gly Asp Val Lys Cys Asp Met
65                  70                  75                  80

Glu Val Ser Cys Pro Asp Gly Tyr Thr Cys Cys Arg Leu Gln Ser Gly
                85                  90                  95
```

```
Ala Trp Pro Trp Cys Glu Gln Gly Pro His Gln Val Pro Trp Met Glu
            100                 105                 110

Lys Ala Pro Ala His Leu Ser Leu Pro Asp Pro Gln Ala Leu Lys Arg
            115                 120                 125

Asp Val Pro Cys Asp Asn Val Ser Ser Cys Pro Ser Ser Asp Thr Cys
        130                 135                 140

Cys Gln Leu Thr Ser Gly Glu Trp Gly Cys Cys Pro Ile Pro
145                 150                 155

<210> SEQ ID NO 6
<211> LENGTH: 96
<212> TYPE: PRT
<213> ORGANISM: Mus musculus

<400> SEQUENCE: 6

Glu Lys Asp Ala Gly Ser Val Gln Pro Ser Met Asp Leu Thr Phe Gly
1               5                   10                  15

Ser Lys Val Gly Asn Val Glu Cys Gly Ala Gly His Phe Cys His Asp
            20                  25                  30

Asn Gln Ser Cys Cys Lys Asp Ser Gln Gly Gly Trp Ala Cys Cys Pro
        35                  40                  45

Tyr Val Lys Gly Val Cys Cys Arg Asp Gly Arg His Cys Cys Pro Ile
    50                  55                  60

Gly Phe His Cys Ser Ala Lys Gly Thr Lys Cys Leu Arg Lys Lys Thr
65                  70                  75                  80

Pro Arg Trp Asp Ile Leu Leu Arg Asp Pro Ala Pro Arg Pro Leu Leu
                85                  90                  95

<210> SEQ ID NO 7
<211> LENGTH: 12
<212> TYPE: PRT
<213> ORGANISM: Homo sapiens

<400> SEQUENCE: 7

Glu Gly His Phe Cys His Asp Asn Gln Thr Cys Cys
1               5                   10

<210> SEQ ID NO 8
<211> LENGTH: 5
<212> TYPE: PRT
<213> ORGANISM: Homo sapiens

<400> SEQUENCE: 8

Arg Asp Asn Arg Gln
1               5
```